(12) United States Patent
Foland et al.

(10) Patent No.: US 7,606,348 B2
(45) Date of Patent: Oct. 20, 2009

(54) TOMOGRAPHIC IMAGING SYSTEMS AND METHODS

(75) Inventors: Andrew D. Foland, Cambridge, MA (US); Richard Franklin Eilbert, Lincoln, MA (US); Boris Oreper, Newton, MA (US); Nikolay Rolshud, Winchester, MA (US); Prabhav Morje, Reading, MA (US)

(73) Assignee: L-3 Communications Security and Detection Systems Inc., Woburn, MA (US)

( * ) Notice: Subject to any disclaimer, the term of this patent is extended or adjusted under 35 U.S.C. 154(b) by 70 days.

(21) Appl. No.: 11/704,893

(22) Filed: Feb. 9, 2007

(65) Prior Publication Data

US 2008/0025461 A1    Jan. 31, 2008

Related U.S. Application Data

(60) Provisional application No. 60/771,758, filed on Feb. 9, 2006, provisional application No. 60/855,565, filed on Oct. 31, 2006.

(51) Int. Cl.
*G01N 23/04* (2006.01)
*G01N 23/083* (2006.01)

(52) U.S. Cl. ............................... 378/57; 378/4
(58) Field of Classification Search .................. 378/4, 378/57, 901
See application file for complete search history.

(56) References Cited

U.S. PATENT DOCUMENTS

| | | | |
|---|---|---|---|
| 4,064,440 A | 12/1977 | Roder | |
| 5,247,561 A | 9/1993 | Kotowski | |
| 5,442,672 A | 8/1995 | Bjorkholm et al. | |
| 5,796,802 A * | 8/1998 | Gordon | 378/8 |
| 5,901,198 A * | 5/1999 | Crawford et al. | 378/57 |
| 6,018,562 A * | 1/2000 | Willson | 378/9 |
| 6,236,709 B1 | 5/2001 | Perry et al. | |
| 6,453,003 B1 * | 9/2002 | Springer et al. | 378/57 |
| 6,473,487 B1 * | 10/2002 | Le | 378/57 |
| 6,597,760 B2 * | 7/2003 | Beneke et al. | 378/57 |
| 7,020,241 B2 * | 3/2006 | Beneke et al. | 378/57 |
| 7,203,276 B2 * | 4/2007 | Arsenault et al. | 378/87 |
| 7,369,642 B2 * | 5/2008 | Eilbert et al. | 378/57 |

OTHER PUBLICATIONS

M. Goitein, "Three dimensional density reconstruction from a series of two-dimensional projections," Nuclear Instruments and Methods, vol. 101 (1972), 509-518.*
Roder, F.L., "Principles, History, and Status of Dual-Energy Computerized Tomographic Explosives Detection," *Journal of Testing and Evaluations*, vol. 13, No. 3, May 1985, pp. 211-216.

* cited by examiner

*Primary Examiner*—Allen C. Ho
(74) *Attorney, Agent, or Firm*—Wolf, Greenfield & Sacks, P.C.

(57) ABSTRACT

A method for operating an inspection system is disclosed in which an item under inspection may be moved between radiation sources and detectors illuminated by the sources. The radiation sources may be positioned such that radiation from at least some of the sources impinge on the radiation detectors, forming acute angles with respect to a plane having a normal direction coinciding with the first direction that are substantially in excess of three degrees. Data accumulated by the radiation detectors may be processed to form a three-dimensional tomographic data image of at least a portion of the item under inspection. The processing may be performed using an algebraic reconstruction technique using an inverse system matrix. The inverse matrix can be derived without first computing a transpose of the system matrix.

25 Claims, 17 Drawing Sheets

ART

– Maximum Likelihood $\mathcal{M}^2$

- Function of density estimates $k$
    - And forward-projected attenuation estimate $X$
- Depends on rays $i$
    - Their measurements x and uncertainty σ
        ≈ σ is known a priori from physics and level of attenuation $$\mathcal{M}^2(\hat{\rho}_k) = \Sigma_i \frac{(X_i(\hat{\rho}_k) - x_i)^2}{\sigma_i^2}$$

- Find set of ρ that minimizes $\mathcal{M}^2$ $$\rho_k \text{ s.t. } \frac{\partial \mathcal{M}^2}{\partial \rho_k} = 0$$

FIG. 3

Iteration

- Solve Iteratively
- Start with a guess (constant density in all voxels) and maximize likelihood cell-by-cell
  - Straightforward but tedious algebra
    - $f_{\ell k}$ = contribution of $\ell^{th}$ ray to $k^{th}$ pixel (mostly 0's)

$$\Delta p_i = \frac{\Sigma_\ell (f_{\ell i}/\sigma_\ell)(1/\sigma_\ell)(x_\ell - \Sigma_k f_{\ell k} p_k)}{\Sigma_\ell f_{\ell i}^2 / \sigma_\ell^2}$$

Essentially: weighted average of discrepancies of all rays passing through pixel

FIG. 4

Relaxation

- Do this $\quad p' = p + \lambda \Delta p$

- How to choose $\lambda$?
    - Minimize $\mathcal{M}^2$ wrt $\lambda$ $\quad \lambda$ s.t. $\frac{\partial \mathcal{M}^2}{\partial \lambda} = 0$
  - Result is (rays $j$ pixels $k$):

$$\lambda = \frac{\Sigma_j (c_j/\sigma_j^2)(x_j - \Sigma_k f_{jk} p_k)}{\Sigma_j (c_j^2/\sigma_j^2)} \quad c_j = \Sigma_k f_{jk} \Delta_{pk})$$

FIG. 5

Section B-B

Section A-A

Section C-C

TOMOGRAPHIC IMAGING SYSTEMS AND METHODS

This application claims the benefit under 35 U.S.C. §119 (e) of each of U.S. Provisional Application Ser. No. 60/771,758, filed Feb. 9, 2006, and U.S. Provisional Application Ser. No. 60/855,565, filed Oct. 31, 2006. The entire contents of each of the foregoing applications is incorporated herein by reference.

BACKGROUND

Inspection systems are widely used to provide security, such as at airports or other facilities, wherever it is desired to create a secured area. Generally, one or more inspection systems are established at a checkpoint. Items passing the checkpoint are inspected to determine whether a weapon, explosive or other contraband is concealed within the item.

It has long been known that penetrating radiation (such as x-rays) may be used to characterize the contents of parcels, luggage, etc. The term "x-rays" refers to electromagnetic radiation of a very short wavelength that is capable of penetrating many objects. An x-ray "beam" may be formed by a device called a "collimator," which effectively absorbs all x-rays except those traveling in the desired beam direction. For example, if an x-ray source produces x-rays that are directed generally toward a collimator having a slit, the x-rays that hit the surface of the collimator will be absorbed, while the x-rays that pass through the slit will form a beam in the shape of a fan, commonly called a "fan beam."

The contents of an item may be characterized by placing an array of x-ray "detectors" on the opposite side of the item from the x-ray source and collimator, and causing the beam of x-rays to pass through the item before impinging upon the detectors. The detector array may, for example, include a planar array of hundreds or thousands of discrete detectors that are intercepted by a cone-shaped x-ray beam, or, as is more common in baggage inspection systems, may include a linear array of detectors that are intercepted by a collimated fan beam. Each detector in an array generates an electronic signal having a magnitude that corresponds to the intensity of the x-rays that impacted it during a "sample interval." Because higher-density materials in the item being scanned will absorb more x-rays than lower-density materials, the signal output by the detectors that are in the "shadow" of higher-density materials will be lower in value than the signal output by those detectors that are intercepted by x-rays that pass only through lower-density materials.

By using a conveyor, e.g., a conveyor belt or a set of rollers, to move an item though the plane of a fan beam, a series of "lines" of x-ray transmission data may be accumulated by a linear array of detectors intercepted by the beam. Each such line of data would represent a sample interval, for the entire array of detectors, taken when the item on the conveyor was at a particular position with respect to the fan beam/detector array. Using these lines of data, an image (i.e., a collection of data that represents the item under inspection) may be generated having a resolution that depends upon the number of detectors in the array, as well as the number of lines of data that were accumulated. As a practical matter, the number of data points, or "pixels," in such an image will be limited by the number of detectors in the array multiplied by the accumulated number of lines of data.

The data points included in an image can represent any of a number of parameters. In some systems, the data points simply represent the intensity values that are measured by the respective detectors. In other systems, the data points represent attenuation measurements that are calculated, for example, by taking the inverse natural logarithm of the ratio of the radiation intensity measured by the detectors to the intensity of the incident radiation. In yet other systems, the data points represent linear density measurements that are determined based upon the calculated attenuation measurements in addition to other known parameters, such as the distance between the source and detectors, according to well-known equations and techniques. In still other systems in which the thickness of the item under inspection can somehow be measured or approximated in the direction of the rays that intersect the item under inspection, the volumetric density of corresponding sections of the item under inspection can also be calculated and used to form data points in an image.

Conventional x-ray scanners frequently determine a linear density at numerous points throughout an item under inspection. Because objects that may be inside the item under inspection frequently have recognizable density profiles, a density image formed with the x-ray scanner can provide useful information about objects inside the item under inspection. In some inspection systems, the density image is presented visually to a human operator. In other systems, computerized systems are used to automatically process the image to identify a density profile that is characteristic of a contraband object.

Images formed by many inspection systems are these types of two-dimensional projection images. Because attenuation of the radiation is related to the density of the material through which the radiation passed, making x-ray projection images in this fashion is useful to detect many types of contraband. For example, rays of radiation passing through a gun, knife or other relatively dense object will be highly attenuated. Each pixel in the image formed by measuring rays passing through such an object will appear very different from other pixels in the image. More generally, contraband objects are likely to appear in the image as a group of pixels having an attenuation different than that of other surrounding pixels. The group will form a region with an outline conforming to the silhouette of the object. Such a group of pixels may be identified as a "suspicious region" based on manual or automated processing if it has a shape and size that matches a contraband item. Densities, or other measured material properties, of the pixels in the group also may be used in the processing to identify suspicious regions.

Inspection systems are not limited to forming images based on density. Any measurable material property may be used to form an image instead of, or in addition to, density. For example, multienergy x-ray inspection systems may measure an effective atomic number, or "$Z_{eff}$," of regions within an item under inspection and may form images based on the effective atomic number measurements. In a dual energy system, for instance, detector samples may be taken for x-rays at each of two discrete energy levels, and an analysis may be performed on the accumulated data to identify the effective atomic number of the portion of the item that was intercepted by the x-rays during the sample interval. This is possible because it is known that the ratio of the intensities of the samples at the two energies is indicative of the effective atomic number.

If no suspicious region is detected in an image of an item under inspection, the item may be "cleared" and allowed to pass the checkpoint. However, if a suspicious region is found in the image, the item may be "alarmed." Processing of an item in response to an alarm may depend on the purpose of the inspection. For example, an alarmed item may be inspected further, destroyed, blocked from passing the checkpoint, or processed in any other suitable way.

Projection imaging is well suited for finding objects that are dense enough and large enough to produce a group of pixels having a recognizable outline regardless of the orientation of the object within the item under inspection. However, projection images are not well suited for reliably detecting objects that have at least one relatively thin dimension. If the thin dimension is parallel to the rays of radiation passing through the item under inspection, the thin object, even if substantially more dense than other objects in the item under inspection will provide little overall attenuation to the rays passing through the item under inspection. Accordingly, there will be no group of pixels in the image that has an attenuation significantly different from other pixels in the image that can be recognized as a suspicious region.

To provide more accurate detection of relatively thin items, some inspection systems are constructed using computed tomography (CT). In a CT scanner, attenuation through an item under inspection is measured from multiple different directions. Frequently, these measurements are made by placing the x-ray source and detectors on a rotating gantry. An item under inspection passes through an opening in the center of the gantry. As the gantry rotates around the item, measurements are made on rays of radiation passing through the item from many different directions. These measurements can be used to compute the volumetric density, or other material property, of the item under inspection at multiple points throughout a plane through which the rays pass. Such a process is commonly called "CT reconstruction." Each of these computed volumetric densities represents one data value of the image, frequently called a "voxel," in a slice through the item. By moving the item under inspection through the opening in the gantry and collecting image data at multiple locations, voxels having values representative of multiple slices through the item may be collected. The voxels can be assembled into a three dimensional, or volumetric, image of the item under inspection. Even relatively thin objects may form a recognizable group of voxels in such a volumetric image.

In constructing an inspection system, projection imaging is desirable because projection images may be formed quickly and inexpensively with relatively simply equipment. CT imaging is also desirable because some objects, such as relatively thin objects, are more reliably detected in volumetric images formed by a CT scanner. However, conventional CT scanners are frequently more expensive and slower than projection scanners. Also, because a conventional CT scanner has more moving parts, it requires more frequent maintenance than a projection imaging system.

Attributes of both a projection imaging system and a CT imaging system may be combined. One example is the MVT™ imaging system sold by L-3 Communications Security and Detection Systems, Inc., of Woburn, Mass. The MVT™ system employs multiple source-detector pairs. Each pair is positioned to form a projection image of an item under inspection from a different angle than the others. The image data gathered by each of the source-detector pairs is analyzed to detect suspicious regions in the image representative of suspicious objects. Data from each image is also used together with data from the other images to facilitate such detection. For instance, data from one image that reveals the thickness of an item can be used in conjunction with linear density measurements reflected in another image to ascertain average volumetric density measurements.

The MVT™ system, like other projection scanners, provides an advantage over a CT system of not requiring a moving source and detectors. Like a CT system, it provides an advantage over a projection imaging system of being able to detect many thin objects. Though a contraband object may have a thin dimension parallel to the rays used to form one of the projection images, a contraband object having any significant size cannot have thin dimensions parallel to the rays used to form all of the x-ray projections. Accordingly, even though a contraband object may not be readily recognizable from one of the projection images formed by the MVT™ system, such a contraband item is likely to be recognizable from at least one of the other projection images.

Nonetheless, it would be desirable to improve the images formed in a system like the MVT™.

SUMMARY

According to one aspect of the present invention, a method for operating an inspection system involves moving an item under inspection in a first direction relative to and at least partially between at least one radiation source and at least some radiation detectors illuminated by the at least one radiation source. The radiation source and detectors are operated such that ray paths extending linearly between the at least one radiation source and at least some of the radiation detectors form acute angles with respect to a plane having a normal direction coinciding with the first direction that are substantially in excess of three degrees. Data accumulated by the radiation detectors is processed to form a three-dimensional tomographic data image of at least a portion of the item under inspection.

According to another aspect, an inspection system comprises a frame, at least one radiation source, radiation detectors, a conveyor, and a processor. The radiation source is supported by the frame and emits rays of radiation. The radiation detectors are supported by the frame and are configured and arranged to detect rays of radiation emitted by the at least one radiation source. The conveyor is configured and arranged to move an item under inspection in a first direction relative to the frame such that at least a portion of the item under inspection passes between the at least one radiation source and at least some of the radiation detectors. The processor is configured to process data accumulated by the radiation detectors to form a three-dimensional tomographic data image of at least a portion of the item under inspection. In addition, the radiation source and the radiation detectors are configured and arranged with respect to the conveyor such that ray paths extending linearly between the at least one radiation source and at least some of the radiation detectors form acute angles with respect to a plane having a normal direction coinciding with the first direction that are substantially in excess of three degrees.

According to another aspect, a method involves accumulating transmission data for rays of radiation that are generated by at least one radiation source and detected by a plurality of radiation detectors, and processing the transmission data to form a tomographic image, in which, for all possible orientations of a three dimensional plane, the orientation vectors of at least some of the rays of radiation for which transmission data was accumulated and used to form the tomographic image form an angle of less than eighty-five degrees or greater than ninety five degrees with respect to the plane.

According to another aspect, the an inspection system comprises at least one radiation source, a plurality of radiation detectors, and a processor. The radiation detectors are configured and arranged to detect rays of radiation that are generated by the radiation source. The processor is configured to process transmission data based upon outputs of the plurality of radiation detectors to form a tomographic image, in which, for all possible orientations of a three dimensional plane, the orientation vectors of at least some of the rays of radiation for which transmission data was accumulated and used to form the tomographic image form an angle of less than eighty-five degrees or greater than ninety five degrees with respect to the plane.

According to another aspect, a method comprises steps of: (a) determining an approximation, other than a multiple of a transpose, of an inverse of a system matrix for an inspection system; (b) after performing the step (a), scanning an item under inspection to accumulate scan data for each of a plurality of rays through the item under inspection; (c) computing an initial estimate of a volumetric image of the item under the inspection by combining the determined approximation of the inverse of the system matrix and the scan data; and (d) employing an iterative process to refine the initial estimate of the volumetric image to obtain a more accurate volumetric image corresponding to the scan data.

According to another aspect, an inspection system comprises means for determining an approximation, other than a multiple of a transpose, of an inverse of a system matrix for an inspection system; at least one radiation source and a plurality of radiation detectors configured and arranged to accumulate scan data for each of a plurality of rays through the item under inspection after the means for determining has determined the approximation of the inverse of the system matrix; means for computing an initial estimate of a volumetric image of the item under the inspection by combining the determined approximation of the inverse of the system matrix and the scan data; and means for employing an iterative process to refine the initial estimate of the volumetric image to obtain a more accurate volumetric image corresponding to the scan data.

According to another aspect, an inspection system comprises means for moving an item under inspection in a first direction relative to and at least partially between at least one radiation source and at least some radiation detectors illuminated by the at least one radiation source; means for operating the at least one radiation source and the radiation detectors such that ray paths extending linearly between the at least one radiation source and at least some of the radiation detectors form acute angles with respect to a plane having a normal direction coinciding with the first direction that are substantially in excess of three degrees; and means for processing data accumulated by the radiation detectors to form a three-dimensional tomographic data image of at least a portion of the item under inspection.

According to another aspect, an inspection system comprises means for accumulating transmission data for rays of radiation that are generated by at least one radiation source and detected by a plurality of radiation detectors; and means for processing the transmission data to form a tomographic image, in which, for all possible orientations of a three dimensional plane, the orientation vectors of at least some of the rays of radiation for which transmission data was accumulated and used to form the tomographic image form an angle of less than eighty-five degrees or greater than ninety five degrees with respect to the plane.

According to another aspect, an apparatus comprises a frame supporting at least first and second skewed radiation sources and at least first and second radiation detectors. The first and second radiation detectors are substantially non-contiguous such that a substantial gap exists between the first and second radiation detectors that is free of any radiation detectors. Each of the first and second radiation detectors is also configured and arranged to detect radiation emitted by each of the first and second skewed radiation sources.

According to another aspect, a method involves moving an item under inspection in a first direction relative to and at least partially between at least first and second skewed radiation sources and at least first and second radiation detectors that are substantially non-contiguous such that a substantial gap exists between the first and second radiation detectors that is free of any radiation detectors. Radiation emitted by each of the first and second skewed radiation sources is detected with each of the first and second radiation detectors.

According to another aspect, an apparatus comprises means for moving an item under inspection in a first direction relative to and at least partially between at least first and second skewed radiation sources and at least first and second radiation detectors that are substantially non-contiguous such that a substantial gap exists between the first and second radiation detectors that is free of any radiation detectors; and means for operating the at least first and second skewed radiation sources and the at least first and second radiation detectors such that each of the first and second radiation detectors detects radiation emitted by each of the first and second skewed radiation sources.

According to another aspect, a system comprises a cathode, a target, one or more switches, and a conductive element. The cathode is configured and arranged to generate an electron beam, and the target is configured and arranged to emit radiation when electrons in the electron beam impact the target after being accelerated by an energy source. The one or more switches are configured and arranged to apply either a first voltage or a second voltage from a power supply between the cathode and the target. The conductive element is disposed between the cathode and the target so as to inhibit the electron beam generated by the cathode from reaching the target when a signal is applied to the conductive element.

According to another aspect, a method involves applying each of a first voltage and a second voltage between a cathode that generates an electron beam and a target that emits radiation when electrons in the electron beam impact the target after being accelerated by an energy source. In addition, a signal is applied to a conductive element disposed between the cathode and the target so as to inhibit the electron beam generated by the cathode from reaching the target.

According to another aspect, a system comprises a cathode configured and arranged to generate an electron beam and a target configured and arranged to emit radiation when electrons in the electron beam impact the target after being accelerated by an energy source. In addition, the system comprises means for applying either a first voltage or a second voltage between the cathode and the target, and means for inhibiting the electron beam generated by the cathode from reaching the target.

BRIEF DESCRIPTION OF THE DRAWINGS

FIG. 3 illustrates an example of a computation that may be performed in connection with computing a volumetric image;

FIG. 4 illustrates another example of a computation that may be performed in connection with computing a volumetric image;

FIG. 5 illustrates another example of a computation that may be performed in connection with computing a volumetric image;

DETAILED DESCRIPTION

Figure 1:
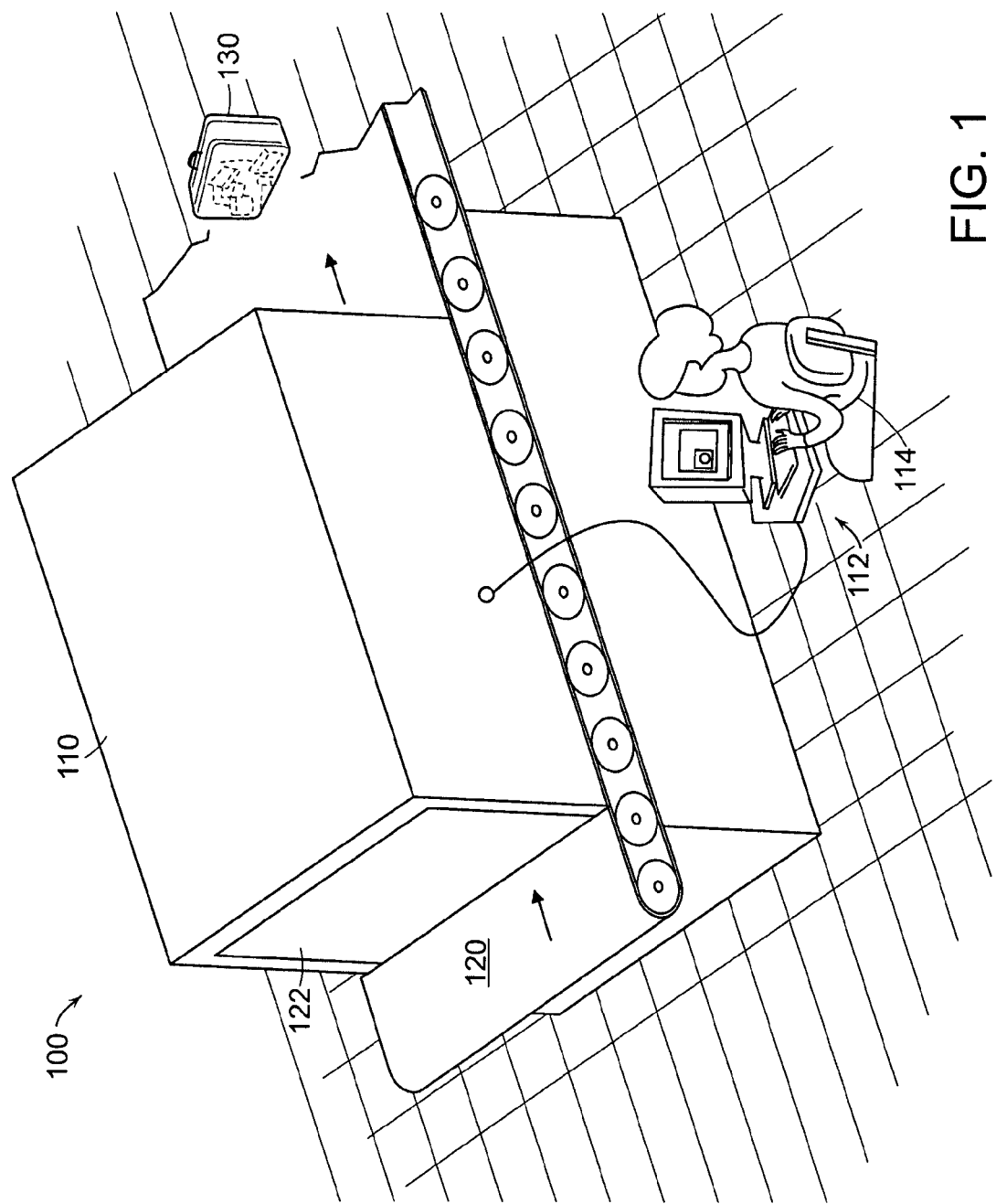
FIG. 1 is a drawing of a security checkpoint employing an example of an inspection system that may embody various aspects of the invention.

FIG. 1 illustrates a security checkpoint 100 at which an inspection system according to various embodiments of the invention may be employed. The checkpoint 100 may, for example, be a checkpoint used at any facility at which it is desired to create a secured area. For instance, at an airport, the checkpoint 100 may be located at the entrance to boarding gates and used to inspect passenger carry on luggage. Alternatively, the checkpoint 100 may be positioned at an airport to inspect checked baggage before it is loaded on airplanes. Inspection systems according to embodiments of the invention are not limited to use at airports, however; the checkpoint 100 may be a checkpoint located in any suitable setting.

In the example shown, the checkpoint 100 includes an inspection system 110. As described in greater detail below, the inspection system 110 may produce volumetric images of items under inspection. In the example of FIG. 1, an item under inspection 130 is pictured as a suitcase. However, the inspection system 110 may operate on any suitable type of item under inspection, such as other forms of luggage, carry on items, parcels or any other container in which contraband objects may be concealed. In some embodiments, the inspection system 110 may even be large enough to examine the contents of cargo containers, cars, trucks, ocean going vessels, etc.

In the embodiment shown, the inspection system 110 includes a conveyor 120. Items under inspection 130 may be placed on the conveyor 120 and moved through a tunnel 122. In alternative embodiments, the x-ray sources and detectors may be moved along the length of an item under inspection while the item remains stationary, or both the item and the sources and detectors may be moved relative to one another during the inspection process. All that is important is that the item under inspection and the source/detector combinations somehow move relative to one another so as to allow the item to be imaged. Within the tunnel 122, x-ray sources (not shown in FIG. 1) are positioned to direct radiation at items on the conveyor 120. Detector arrays (also not shown in FIG. 1) are positioned to receive radiation from the x-ray sources after the radiation has passed through an item under inspection.

Data output from the detectors can be used to form an image of the item under inspection which may then be analyzed. For example, outputs of the detector arrays may be passed to a computer 112, which may process the outputs of the detectors to form a volumetric image of each item under inspection. Each such volumetric image may then be analyzed to detect suspicious regions within the image.

Image analysis may, for example, be performed by displaying a visual representation of the image for examination by a human operator 114. Additionally or alternatively, the computer 112 may process the volumetric images using automatic detection algorithms to identify suspicious regions. Once suspicious regions are identified by computer processing, those regions may be highlighted in a visual image displayed for the human operator 114.

In the embodiment illustrated, the computer 112 is shown as a desktop computer workstation located at the checkpoint 100. However, the type and location of the computer 112 is not a limitation on the invention. For example, the computer 112 may alternatively be integrated into the chassis of the inspection system 110, or may be connected to the inspection system 110 over a network link. If the computer 112 is connected over a network link, it may be located at any suitable location reachable by the network and does not need to be physically located at the checkpoint 100. Further, although the computer 112 is shown as a single computer, it should be appreciated that a collection of one or more computers may alternatively be used to process data collected by the inspection system 110. If processing is performed by multiple computers, it is not necessary that the computers be located together. Accordingly, the computer 112 should be understood to represent one or more computer processors located in any suitable location or locations that may perform processing on the data collected by the inspection system 110.

Figure 2:
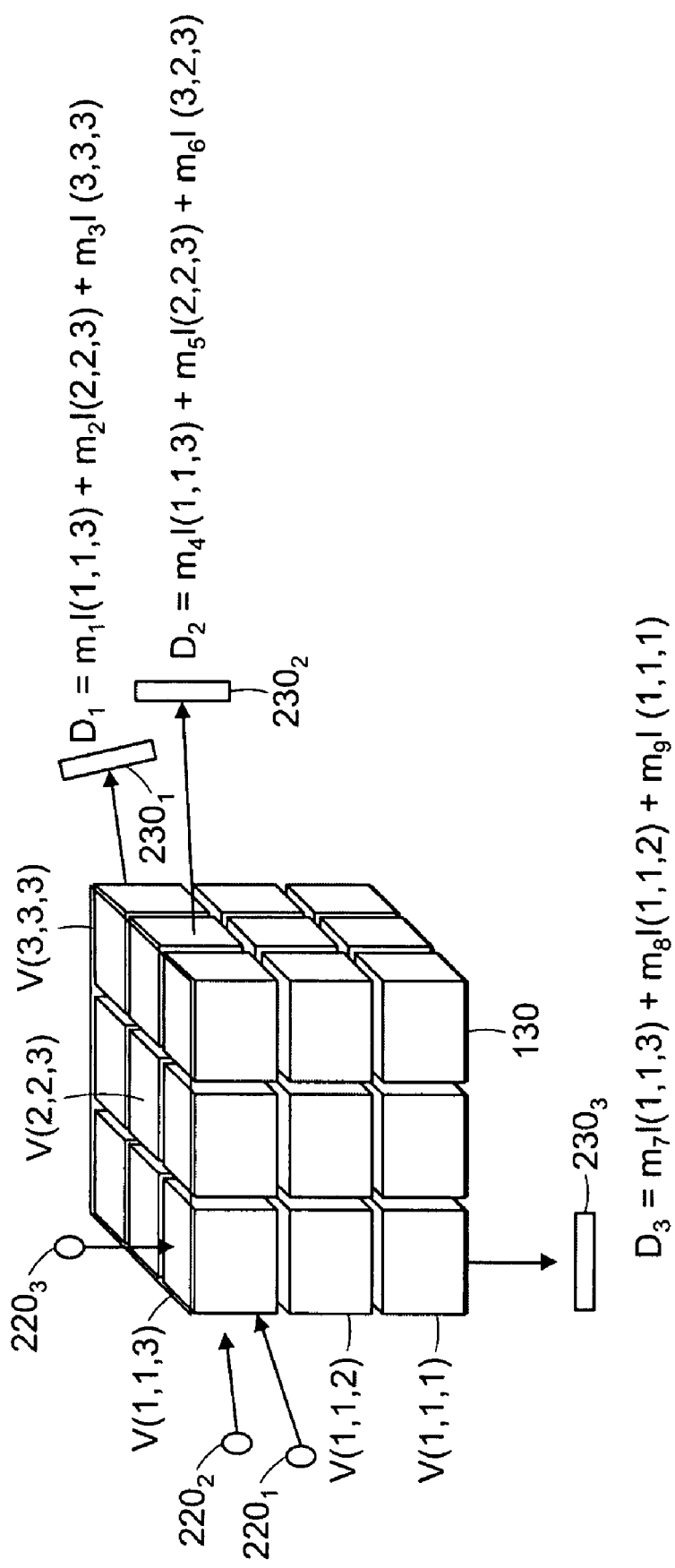
FIG. 2 is a diagram illustrating an example of a technique for forming a multiview volumetric image.

FIG. 2 is an illustration demonstrating how a volumetric density image may be computed from measurements made on an item under inspection 130 by an inspection system such as that shown in FIG. 1. In the simple example of FIG. 2, the item under inspection 130 is divided into twenty-seven regions. An image of the item under inspection 130 may be formed by computing a property of the material in each of these twenty-seven regions. Each of the twenty-seven regions will correspond to a voxel in the computed image. For this reason the regions in the item under inspection are sometimes also referred to as "voxels." In the simple example of FIG. 2, the item under inspection 130 is divided into twenty-seven voxels of which voxels V(1,1,1), V(1,1,2), V(1,1,3), V(2,2,3) and V(3,3,3) are numbered. To form an image of the item under inspection 130, a material property may be computed for each of the voxels from the measured outputs of detectors. In the illustrated embodiment, the material property is the volumetric density of the material within each voxel.

In the example shown, measurements from which the volumetric densities of the respective voxels may be computed are made by passing rays of radiation through the item under inspection 130 from different directions. By using detectors $230_1$, $230_2$, $230_3$ to measure the intensity of the rays after they have passed through the item under inspection and comparing the measured intensity to a known incident intensity, attenuation measurements (e.g., $D_1$, $D_2$, and $D_3$ in FIG. 2) may be made. For example, each attenuation measurement $D_i$ for a corresponding ray may be calculated according to the following equation:

$$D_i = -\ln(\text{INT}_{measured}/\text{INT}_{incident}).$$

In this equation, $\text{INT}_{measured}$ represent the intensity of the $i^{th}$ ray measured by a corresponding detector, and $\text{INT}_{incident}$ represents the intensity the incident ray before it was intercepted the item under inspection, which is a known value. When attenuation measurements $D_i$ are made along a sufficient number of rays traveling in a sufficient number of directions, the data collected can be processed to compute the volumetric density within each of the voxels individually.

Processing may be performed, for example, by treating each attenuation measurement $D_i$ as defining one equation of a system of simultaneous equations in which the volumetric densities of the voxels are unknowns. Computing the image may thus involve solving the system of simultaneous equations for the unknown values of the volumetric voxel densities.

For example, FIG. 2 shows a source $220_1$ and a detector $230_1$. A ray traveling from the source $220_1$ to the detector $230_1$ passes through voxels V(1,1,3), V(2,2,3) and V(3,3,3). As a result, the attenuation measurement $D_1$ that is determined based on the output from the detector $230_1$ will depend on the volumetric densities of each of those three voxels. That attenuation measurement $D_1$ may be expressed as an equation:

$$D_i = m_1 I(1,1,3) + m_2 I(2,2,3) + m_3 I(3,3,3).$$

In this equation, I(1,1,3) represents the volumetric density within voxel (1,1,3). Similarly, each of the other values express as a function of I( ) represents the volumetric density within a corresponding voxel.

Each of the quantities $m_1$, $m_2$ and $m_3$ represents a weighting factor indicating the manner and amount that the corresponding voxel influences the attenuation measurement $D_1$ made by the detector $230_1$. Each weighting factor may represent many parameters of the inspection system. For example, for voxels that fall along a ray between the source $220_1$ and the detector $230_1$ that leaves the source $220_1$ at an angle in which the source $220_1$ emits a relatively low amount of radiation, the weighting factors may be relatively small to account for the fact that the quantity $D_1$ will have a disproportionately small value for that reason. Another parameter that may be reflected in a weighting factor is the percentage of the path between a source and a detector that is occupied by a corresponding voxel. For example, if a ray between the source $220_1$ and the detector $230_1$ passes through all of the voxel V(1,1,3) but only through a corner of the voxel V(2,2,3), the volumetric density of the voxel V(1,1,3) would have a greater impact on the attenuation measurement $D_1$ determined by the detector $230_1$ than would the volumetric density of the voxel (2,2,3). To reflect this difference in impact, the weighting factor $m_1$ may be made larger than the weighting factor $m_2$. The weighting factors may also reflect the appropriate conversion between attenuation and volumetric density.

In the example of FIG. 2, a ray from the source $220_1$ to the detector $230_1$ represents just one of the rays passing through the item under inspection 200. Other rays are also depicted. For example, a ray is shown passing from the source $220_2$ to the detector $230_2$. As with the ray passing from the source $220_1$ to the detector $230_1$, an equation can be written representing the attenuation measurement $D_2$ as determined from the output of the detector $230_2$. In this case, the ray from the source $220_2$ to the detector $230_2$ passes through the voxels V(1,1,3), V(2,2,3) and V(3,2,3). Accordingly, the equation for the attenuation measurement $D_2$ is given by:

$$D_2 = m_4 I(1,1,3) + m_5 I(2,2,3) + m_6 I(3,2,3)$$

The equation for the attenuation measurement $D_2$ is thus in the same form as the equation for the attenuation measurement $D_1$. However, the equation expresses a relationship between volumetric density values for different voxels, and also uses different weighting factors than those that are used to describe the attenuation measurement $D_1$. Specifically, the equation describing the attenuation measurement $D_2$ uses volumetric density values I(1,1,3) I(2,2,3), and I(3,2,3) for voxels V(1,1,3), V(2,2,3) and V(3,2,3), and weighting factors $m_4$, $m_5$ and $m_6$.

A similar equation can be written representing the attenuation measurement $D_3$ as determined from the output of the detector $230_3$. In the illustrated embodiment, the attenuation measurement $D_3$ depends on the amount that a ray passing from the source $220_3$ to the detector $230_3$ is influenced by the volumetric densities of the voxels along that ray, as well as the weighting factors representative of parameters of the inspection system. Such an equation, though in the same form as equations for $D_1$ and $D_2$, will include volumetric density values for different voxels and may contain different weighting factors.

FIG. 2 shows only three rays passing through the item under inspection 130. Each of the rays generates one equation containing as unknowns values representative of the volumetric densities of a particular set of voxels in the item under inspection 130. From basic linear algebra, it is known that a system of equations may be solved if the number of independent equations equals or exceeds the number of unknowns. In the simple problem illustrated in FIG. 2, the item under inspection 130 is divided into twenty-seven voxels. Accordingly, at least twenty-seven independent equations are required to solve for the volumetric density in each of those twenty-seven voxels. Accordingly, though FIG. 2 shows only three rays passing through the item under inspection 130, to compute a volumetric image of the item under inspection 130, measurements on at least twenty-seven rays passing through the item under inspection 130 from different angles would be needed.

If a sufficient number of attenuation measurements $D_i$ along rays from a sufficient number of independent angles are made, the measured outputs of the detectors may be used to define a system of simultaneous equations that may be solved for the unknown values representing the volumetric densities of the individual voxels in the item under inspection 130. Such a system of simultaneous equations may be represented by a matrix equation in the form:

$$I*M = D$$

In this equation, "I" represents a vector containing the unknown values of the volumetric densities of the voxels, which needs to be computed to form an image of the item under inspection 130. In the example of FIG. 2, in which twenty-seven voxels are shown, the vector I will have twenty-seven entries. However, FIG. 2 represents a simplified example and, in a practical system, the vector I may have many more than twenty-seven entries.

The value "M" in the above equation is a matrix representing the collection of the weighting factors $m_1$, $m_2$ ... Because the values of the weighting factors are determined by parameters of the system, such as the position and operating characteristics of the sources and detectors used to take the various measurements, these values may be determined. The values in the matrix M may be computed based upon known properties of the inspection system 110 or may be determined empirically. As one example, the weighting factors may be determined empirically, for example, by taking measurements using the system with one or more items having known properties.

The quantity "D" represents a vector containing the attenuation measurements as determined using the outputs of respective detectors. The value of D is thus also known after an item has been scanned by the system 110.

Accordingly, the image I may be computed by solving the above equation. Conceptually, the vector I may be computed by multiplying both sides of the equation by the inverse of the matrix M. This operation is represented by the equation:

$$I = D * M^{-1}$$

For an inspection system, such as the inspection system 110, this equation indicates that the image vector I of item under inspection 130 may be computed by multiplying a vector containing attenuation measurements as determined using the outputs of multiple detectors by the inverse of a matrix M containing values characterizing the measurement system.

In a physical system, the number of measurements taken will likely exceed the number of voxels in the image. Uncertainty or other variations in the measurement process may prevent a single solution from satisfying simultaneously all equations in a system of equations formed from the measurements. Thus, solving the system of equations formed from actual measurements may involve finding the values that best solve the equations.

With respect to the above discussion, it should be appreciated that, in lieu of the attenuation measurements $D_i$, other measured values, such as linear density measurements, or even simply detector output values representing the measured intensities of respective rays, may alternatively be used in the above equations provided that the weighting factors in the system matrix M are appropriately adjusted to account for such a substitution.

FIG. 3 illustrates an example of an algebraic reconstruction technique (ART) which may be employed as a direct method of computing a value ρ for each of the voxels in the item under inspection. The illustrated equations and technique are explained in more detail in M. Goitein, "Three Dimensional Density Reconstruction from a Series of Two-Dimensional Projections," Nuclear Instruments and Methods, Volume 101, pp. 509-518 (1972), which is incorporated herein by reference in its entirety. Additional details concerning possible implementations of such a technique are also described in U.S. Pat. Nos. 5,442,672 and 6,236,709, each of which is incorporated herein by reference in its entirety. The process of FIG. 3 illustrates that a maximum likelihood estimate, represented as $M^2$, may be computed. In the equation, $X_i$ is a function of the voxel densities yielding an estimate of values measured along the $i^{th}$ ray. By subtracting this estimate from the actual measured value , $\chi_i$, an error value is obtained. When these error values are weighted by an uncertainty value $\sigma_i$, squared and summed with similarly computed values along other rays, a value of $M^2$ results. Density values can be computed that minimize the changes in $M^2$ with respect to changes in density values. Density values that satisfy this criteria represent the computed image.

Solving an equation of linear algebra through use of an inverse technique is sometimes referred to as a "direct" method of computing the image. While computing the image vector I by a direct method would involve a relatively straight forward application of linear algebra techniques, direct methods have not been used in practice. One reason deterring the use of direct methods is that the system matrix M typically varies with time. Noise, electronic drift and other variables may alter the weighting factors that define the system matrix M. A further deterrent to the use of direct methods is the amount of computation involved in computing the inverse of matrix M. The image vector I may have thousands, or tens of thousands, of entries. The system matrix M will have a number of entries that is proportional to the square of the number of entries in the image vector I and therefore may have billions of entries. Even if the matrix M can be readily determined, using an inverse technique is a computationally difficult task that prevents the direct method from being used in a practical inspection system in which items must be cleared or alarmed within a finite, and usually very short, period of time.

FIG. 4 represents an alternative approach to finding values that maximize the likelihood that an image vector solves a system of equations developed from measurements of radiation passing through an item under inspection. The equations and approach illustrated in this figure are explained in more detail in M. Goitein, "Three Dimensional Density Reconstruction from a Series of Two-Dimensional Projections," Nuclear Instruments and Methods, Volume 101, pp. 509-518 (1972), incorporated by reference above. This approach may be used, for example, for computing volumetric density values that form an image of the item under inspection. In the approach of FIG. 4, the equations defining the relationship between the attenuation measurements and the volumetric density values of the voxels of the items under inspection are solved iteratively.

The iterative solution starts with an initial guess of the vector representing the volumetric densities of the voxels. In the example of FIG. 4, a constant density in each voxel is used as an initial estimate of the image vector. Thereafter, values of the densities in each of the voxels are computed iteratively by finding values that maximize the likelihood that the computed density values correctly solve the system of equations derived from the attenuation measurements determined by the detectors. At each iteration, a discrepancy of the estimated value of the vector ρ is computed. This discrepancy is depicted in FIG. 4 by the quantity $\Delta\rho_i$.

The discrepancy vector $\Delta\rho$ may be used to compute the estimated value of ρ for the next iteration, which in FIG. 5 is denoted ρ'. As shown in FIG. 5, the value of ρ' is computed as the sum of ρ, the prior estimate of the density vector, plus the discrepancy value $\Delta\rho$ multiplied by a relaxation value λ.

Using a relaxation value λ prevents the iterative computation from diverging or oscillating. A relaxation value λ may be selected in any suitable way. FIG. 5 shows an example of a suitable equation for computing λ.

Figure 6:
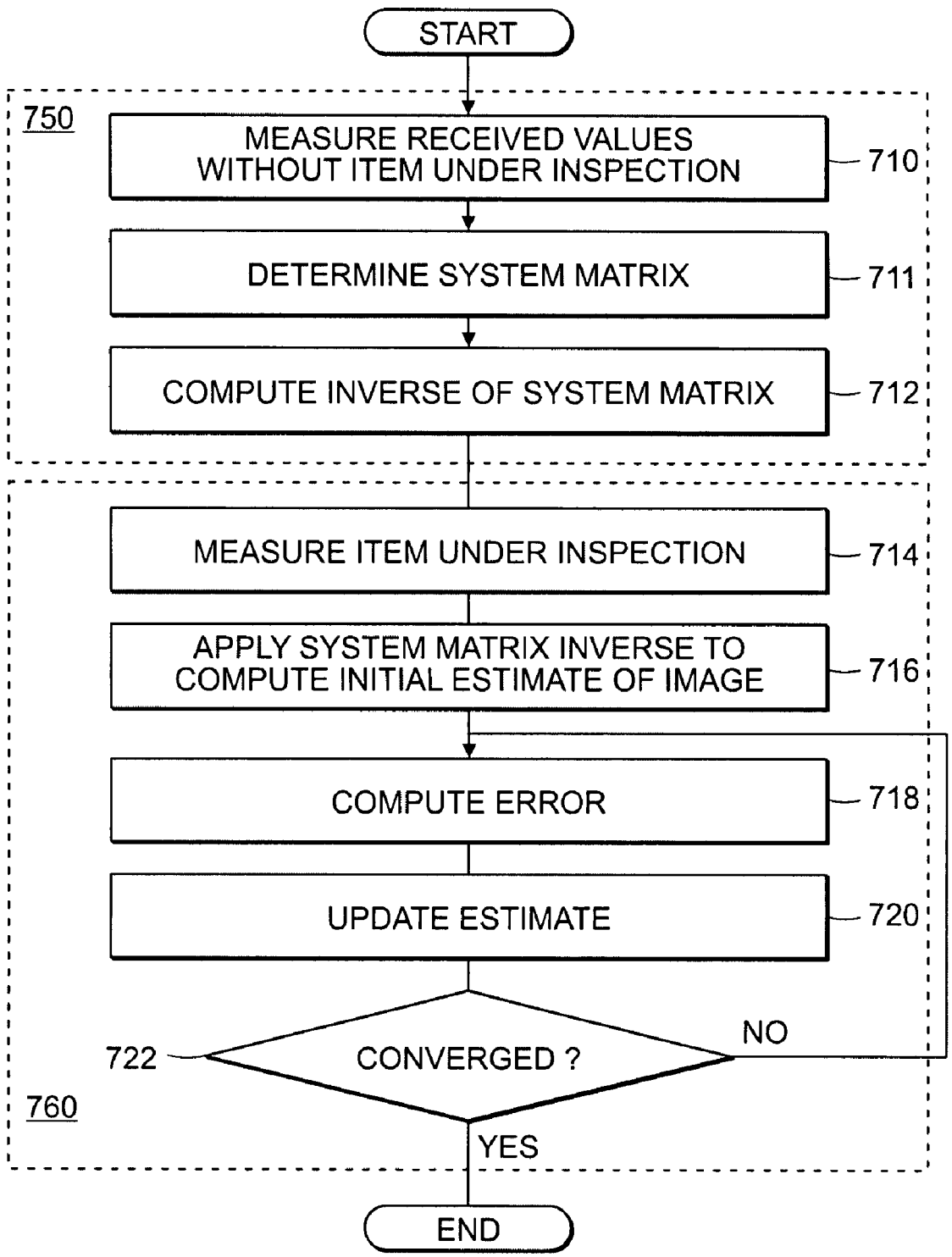
FIG. 6 is a flow chart illustrating an illustrative example of a process that may be used to compute a volumetric image.

Turning to FIG. 6 an alternative embodiment of an iterative process for computing the image vector of an item under inspection is shown. As shown, the process may contain two subprocesses, an off-line subprocess 750 and inspection subprocess 760. The subprocess 750 may be performed "off line," meaning that it can be performed when the inspection system is not actively being used to inspect items. The offline subprocess 750 may, for example, be performed as part of the manufacture of the inspection system. Alternatively, it may be performed as part of the installation of the inspection system or may be performed on a routine or periodic basis as part of a calibration or maintenance routine for the system. Accordingly, the specific time at which offline subprocess 750 is performed is not a limitation of the invention.

Regardless of when the off line subprocess 750 is performed, measurements taken during the subprocess 750 may be used to compute a close approximation of the inverse of system matrix M. As shown in FIG. 6, the off line subprocess 750 may begin at a step 710, where attenuation measurements $D_i$ may be made based upon detector output values without an item under inspection present. Computation to the system matrix M may then be performed at a step 711. Any suitable computational approach may be used to determine the system matrix M. The computation at the step 711 may, for example, be based in whole or in part on the measurements taken at the step 710. Computation may also involve, in whole or in part, computations based on the design of the system. If computation of the system matrix M is based entirely on the design of the system, then the measurements at the step 710 would not be required.

Regardless of how values are obtained to form the system matrix M, at the step 712, the approximation of the inverse of the system matrix M may be computed. Any suitable method may be used to compute the inverse matrix $M^{-1}$. In some embodiments, for example, the inverse matrix $M^{-1}$ may be computed in a computer data processor. As one example, the inverse matrix $M^{-1}$ may be computed by decomposing the matrix M into an upper and lower triangular matrix and then backsubstituting the unit vectors. However, any suitable processing approach may be used.

Regardless of how the approximation of the inverse of the system matrix is computed at the step 712, processing proceeds to a step 714. The processing at the step 714 begins the subprocess 760 (mentioned above), which may be performed for each item under inspection. At the step 714, attenuation measurements $D_i$ may be made on the item under inspection. As described above in connection with FIG. 2, such measurements may be made along a sufficient number of rays passing through the item under inspection from a sufficient number of angles to generate a system of equations that can be solved for the image values at each of the voxels in the item under inspection. In the illustrated embodiments, each image value represents the volumetric density of the item under inspection in a particular voxel.

Once attenuation measurements $D_i$ are collected, processing may proceed to a step 716 where an initial estimate of the image vector I may be computed. At the step 716, the approximated inverse of the system matrix $M^{-1}$ that was computed during the off line process 750 may be applied to the measured attenuation values $D_i$ to provide an initial estimate of the image vector I. Because the approximation of the inverse of the system matrix M may be computed as part of the offline subprocess 750, a time-consuming direct technique to compute the initial estimate of the image vector I can be employed without adversely impacting the on-line throughput of the system. Further, because the result of applying the approximated system matrix inverse $M^{-1}$ is only an initial estimate of the image vector I, any imprecision introduced by variations in the inspection system after the system matrix M has been computed would not necessarily impact the final result. Because the initial estimate is likely to be a close approximation to the actual image values, however, the iterative processing based on that initial estimate of the image vector I may require a relatively small number of iterations to converge to an acceptable solution. Accordingly, with such an initial estimate, the iterative processing in the subprocess 760 may quickly produce an accurate result.

At a step 718 of the on-line subprocess 760, an estimate of the error in the estimated image vector I may be determined. Any suitable approach for computing the error in the estimate may be used for this purpose, and the invention is not limited to the use of any particular technique or approach. In some embodiments, for example, an error may be computed by comparing a "forward projection" of the estimated image vector I to actual attenuation measurements. The forward projection is a computation of the attenuation measurements $D_i$ that would result if the item under inspection had the material characteristics indicated by the estimated image vector I.

Once the initial estimate is computed, processing may proceed to a step 720, where the estimated image vector I may be updated. Any suitable computational technique for iteratively solving a system of equations may be used to update the estimate at the step 720. In some embodiments, for example, the computed error may be used to compute an adjustment to the image vector I that should cause the forward projection to more closely match the actual attenuation measurements $D_i$. The amount of the adjustment may, for example, be proportional or otherwise related to the error.

At a decision step 722, the process branches depending on whether the computation has converged to an acceptable solution. Any suitable method may be used to determine whether the computation of the image vector I has converged. For example, the process may be deemed to have converged if the computed error is below a threshold. Alternatively, convergence may be determined based on the magnitude or percentage change from one iteration to the next.

If it is determined that the processing has not converged, the process loops back to the step 718 where the error in the estimate of the image vector I may again be computed. Processing at the steps 718, 720 and 722 may thus be repeated until it is determined that the updated estimate represents an acceptable solution. When it is determined at the decision step 722 that the iterative computation in the subprocess 760 has converged to an acceptable solution, the process may terminate, with the most recent estimate of the image vector I representing the computed image vector I. The image vector I may thereafter be used to alarm or clear the item under inspection, or used for any other desired purpose.

Figure 7:
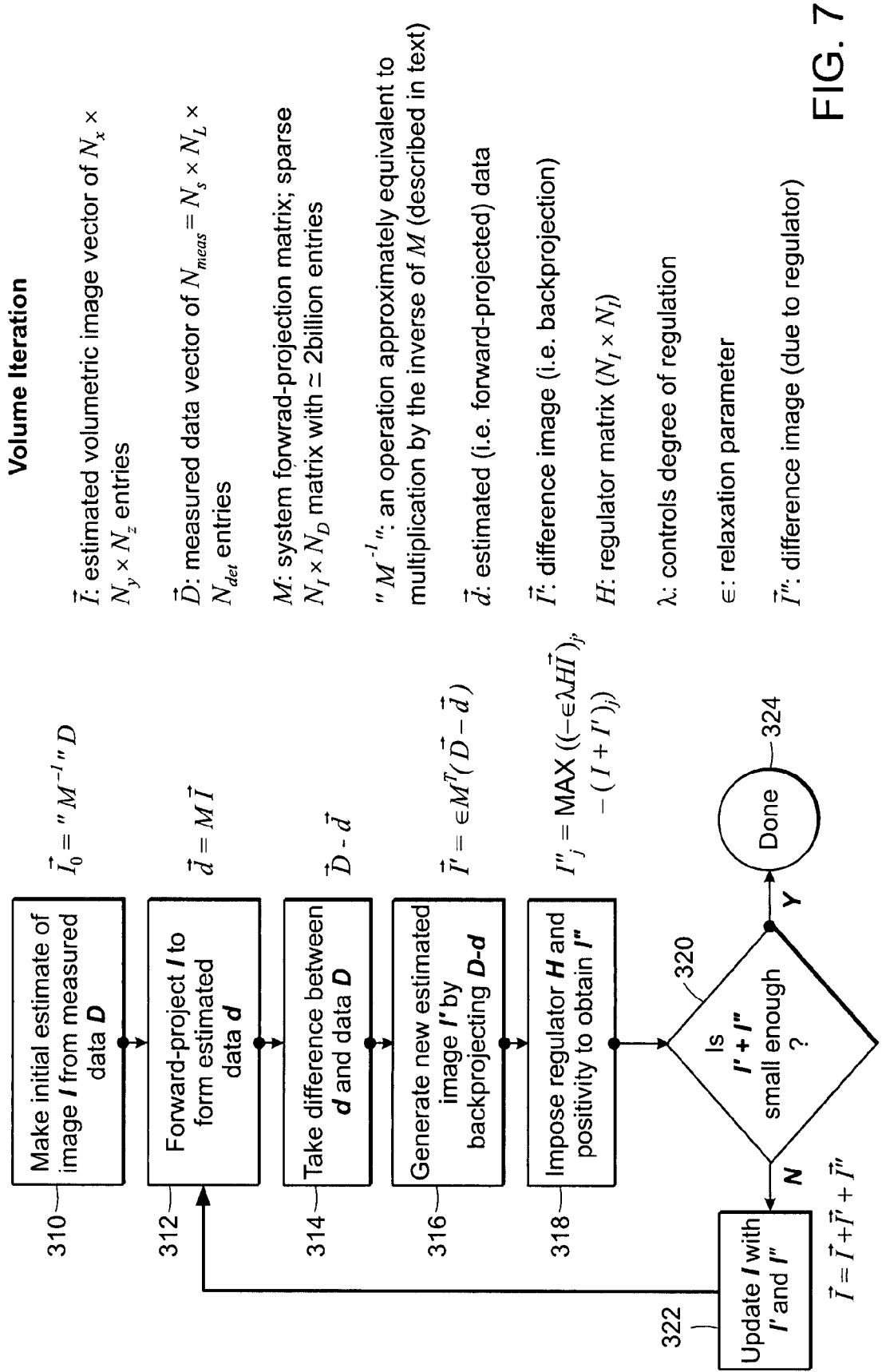
FIG. 7 is a flow chart illustrating another illustrative example of a process that may be used to compute a volumetric image.

The on-line subprocess 760 may involve any suitable computational method. FIG. 7 illustrates, in greater detail, an example of one possible implementation. In particular, FIG. 7 is a flow chart of an example of a process for computing image values using volume iteration. As shown, the process begins at a step 310 where an initial estimate of the image vector I is formed. In FIG. 7, the initial estimate is represented by the value $\vec{I}_o$. In the example shown, the initial estimate $\vec{I}_o$ is computed by multiplying the vector $\vec{D}$, representing the vector of attenuation measurement $D_i$ as determined by outputs of the detectors, by the inverse of a system matrix M. The system matrix M maybe the same as described in connection with FIG. 2 and may represent parameters of the inspection system. However, because the value of the inverse matrix $M^{-1}$ is used only for the computation of an initial estimate, an approximation to the inverse of the current system matrix may instead be used. The inverse matrix $M^{-1}$ may be an approximation either because the values used to form the matrix M are estimates or because the inverse of the matrix M is estimated.

Once the initial estimate of the image vector is determined, an iterative process may be performed to update the initial estimate of the image vector to more accurately match the measured values. Any suitable iterative technique may be used to update the estimate of the image vector, and the invention is not limited to any particular method or technique. The process is shown in FIG. 7 is just one example of a suitable technique.

The process continues to step 312 where a forward projected value $\vec{d}$ may be computed. As shown, the forward projected value $\vec{d}$ may be, for example, be computed by multiplying the estimated image vector $\vec{I}_O$ by the system matrix M.

At a step 314, the difference between the actual attenuation measurements $D_i$ and the forward projected values may be computed. That computation is represented in FIG. 7 by the vector subtraction $\vec{D} - \vec{d}$.

At a step 316, a first image offset component, denoted I', may be computed. As shown, the image offset I' may, for example, be computed by multiplying the difference $(\vec{D} - \vec{d})$ by the transpose of the system matrix, $M^T$, and that product may be scaled by a value $\epsilon$, which acts as a relaxation parameter.

At a step 318, a second difference image component I", may be computed, for example, using a regulator matrix H. The regulator matrix H may be selected using conventional numeric processing methods or in any other suitable way. The value of I" may, for example, be the maximum of (1) the product of the regulator matrix H and the estimate of the image vector I scaled by both the relaxation parameter $\epsilon$ and the parameter $\lambda$, which controls the degree of regulation, and (2) the sum of the estimated image and the difference image I'. In the example shown, both of these values are negated, which should result in positive values, and the larger of the two is selected as the second difference image component I", which for the $j^{th}$ iteration is represented by $I_j"$.

The process continues to a decision step 320. At the decision step 320, the process branches based on whether the sum of the difference images I' and I" is small enough. In this context, what value is "small enough" may be determined in any suitable way. For example, an absolute numeric value may be computed in advance to represent an acceptable level of uncertainty in the values of the computed image. If the sum of the difference images I' and I" is less than the acceptable level of uncertainty, the sum may be accepted as small enough. Alternatively, the numeric value corresponding to values that are small enough may be determined dynamically, as a percentage of the value of the estimated image I, or in any other suitable way.

Regardless of how a specific value is determined, if the sum of the difference images I' and I" is less than that value, the process of FIG. 7 may be deemed to have converged. If the computation has converged, the process branches to a termination point 324 where the process ends with the last estimate of image vector I being used as the computed image vector. However, if the process has not converged, based on the determination made at the decision step 320, the process branches to a step 322. At the step 322, the estimate of the image vector I is updated by adding the difference images I' and I" to it. This updated estimate of the image vector I is then used for a further iteration in the process. Accordingly, FIG. 7 shows the process branching back to the step 312, where the process of computing a further iteration of the image vector I is repeated.

As described in connection with FIG. 2, computing an image vector I from the measured outputs of detectors in an inspection system requires that the detectors measure attenuation along multiple rays passing through the item under inspection from multiple angles. In the embodiment of FIG. 2, for simplicity of illustration, each detector was shown receiving a ray emanating from a separate source. In constructing an inspection system, it is desirable to reduce the number of both sources and detectors used. Accordingly, radiation sources and detectors may be positioned so that multiple detectors receive rays from the same source.

Figure 8A:
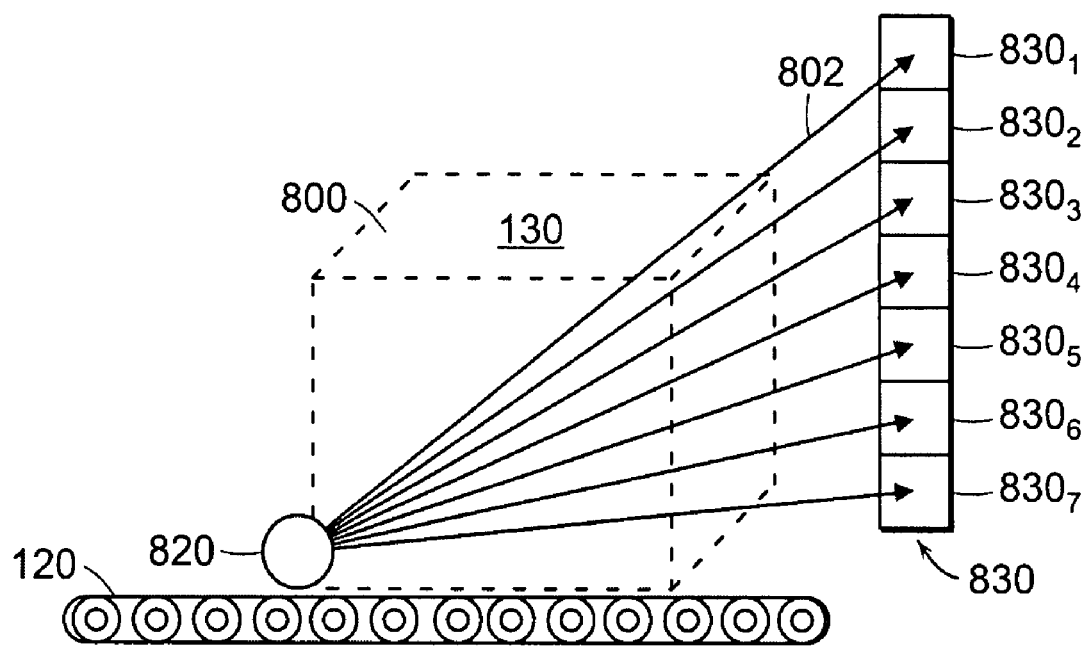
FIGS. 8A, 8B, and 9A-E are drawings illustrating examples of various configurations and techniques that may be used to make attenuation measurements of an item under inspection.

FIG. 8A illustrates an example of a detector array 830 containing detectors $830_1, 830_2 \ldots 830_7$. The detector array 830 may, for example, be positioned on the opposite side of a tunnel (e.g., the tunnel 122 in FIG. 1) as the source 820. As shown, the source 820 may be collimated to emit radiation in a beam 802 containing multiple rays that impinge upon the detector array 830. Accordingly, measuring the outputs of each of the detectors $830_1, 830_2 \ldots 830_7$ while the source 820 is emitting radiation allows attenuation measurements $D_i$ to be made for multiple rays that intersect the portion of the item under inspection 130 through which the beam 802 passes.

Figure 8B:
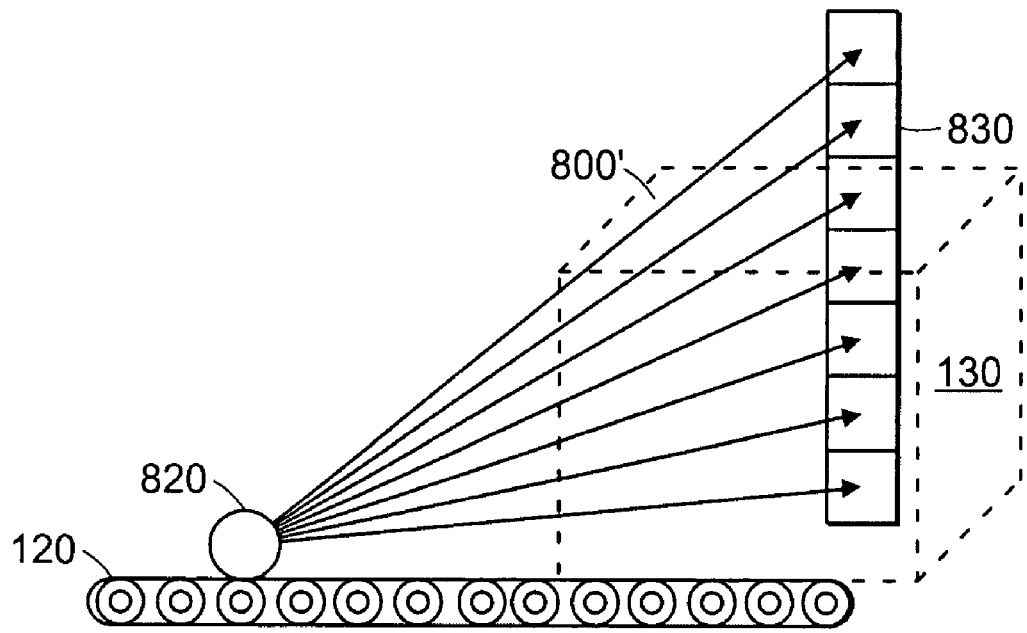

FIG. 8B illustrates how motion of a conveyor 120 may allow additional attenuation measurements $D_i$ to be made along different rays through the item under inspection 130 without moving the source 820 or detector array 830. In FIG. 8A, when the item under inspection 130 was in a first position 800 at a first time, the source 820 and the detector array 830 allowed a first set of attenuation measurement $D_i$ to be made for a first set of rays that intersected a first portion of the item under inspection at the first time. As shown in FIG. 8B, the source 820 and detector array 830 may be kept in the same position as in FIG. 8A, but the conveyor 120 may move the item under inspection 130 from the first position 800 to a second position 800' relative to those components. Accordingly, when the item under inspection 130 is in the second position 800' at a second time, the source 820 and detector array 830 can make a second set of attenuation measurements $D_i$ for a second set of rays that intersect a second portion of the item under inspection 130 at the second time. In this manner, the same source 820 and detector array 830 pair can be used to make discrete attenuation measurements for multiple rays through the item under inspection 120 at multiple times as the item under inspection 130 is moved relative to them.

In an inspection system, a single source and a corresponding detector array may be used to make attenuation measurements $D_i$ for rays passing through the item under inspection over a range of angles. For example, the configuration illustrated in FIGS. 8A and 8B would be capable of making attenuation measurements for rays passing through the item under inspection over a range of angles of approximately 45°. For accurate reconstruction, it may be desirable to have rays passing through the item under inspection from a range of angles that exceeds 180°, or an angle that is as close to 180° as possible. FIGS. 9A-E illustrate source and detector arrangements that may be used to increase the angular range of the rays for which attenuations measurements may be made on an item under inspection.

Figure 9A:
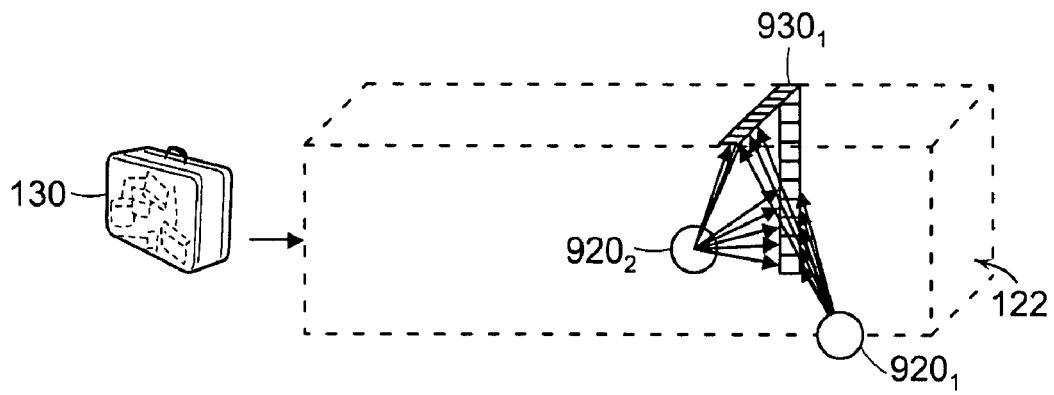

As shown in FIG. 9A, a detector array $930_1$ may have segments that span multiple sides of a tunnel 122. In the example shown, the detector array $930_1$ is an L-shaped array. By using an L-shaped array, or similar array that covers a greater angular extent of the tunnel 122, the angular range over which measurements can be made can be increased without increasing the number of sources. In various embodiments, any or all of the detector arrays in an inspection system may employ such a configuration.

FIG. 9A also illustrates that range of angles through which attenuation measurements may be made can be increased without increasing the number of detector arrays by positioning multiple sources to emit radiation towards the same detector array. In the illustrated example, two sources $920_1$ and $920_2$ are both positioned to emit respective beams of radiation towards the detector array $930_1$. As shown, the sources $920_1$ and $920_2$ may be "skewed," meaning that each source is configured and arranged so as to emit a beam of radiation towards the detector array $930_1$ over a different range of angles than the other. By controlling the sources $920_1$ and $920_2$ so that they to emit their beams of radiation toward the detector array $930_1$ at different times, the detector array $930_1$ can be used to make attenuation measurements based on the rays received from each such source.

In various embodiments, any or all of the detector arrays in the system may be illuminated by two or more skewed sources in this manner. In some embodiments, two or more sources that emit radiation toward a common detector array may be skewed with respect to one another and may also be located in substantially the same plane (perpendicular to the direction of travel of the conveyor) as the detector array. In other embodiments, one or more of such skewed sources may be located in a substantially different plane than the common detector array. In some embodiments, one or more of the sources may be positioned so that rays between the source and at least some of the detectors in the array form an angle with respect to the plane in which the detector array is disposed (perpendicular to the direction of travel of the conveyor) that is substantially in excess of three degrees, or substantially in excess of five degrees, or substantially in excess of ten degrees, or substantially in excess of twenty degrees, or substantially in excess of thirty degrees.

As explained below in more detail, any number of detector arrays, such as the detector array $930_1$, may be included in an inspection system, and each such detector array can be used to detect radiation from multiple sources that emit radiation during distinct time intervals. Each attenuation measurement made by the detectors in each such detector array during the respective time intervals corresponds to an attenuation measurement for a different ray through the item under inspection 130. The collection of the attenuation measurements for any or all of such rays may be used to determine a volumetric image of the item under inspection using the techniques discussed above or otherwise.

Figure 9B:
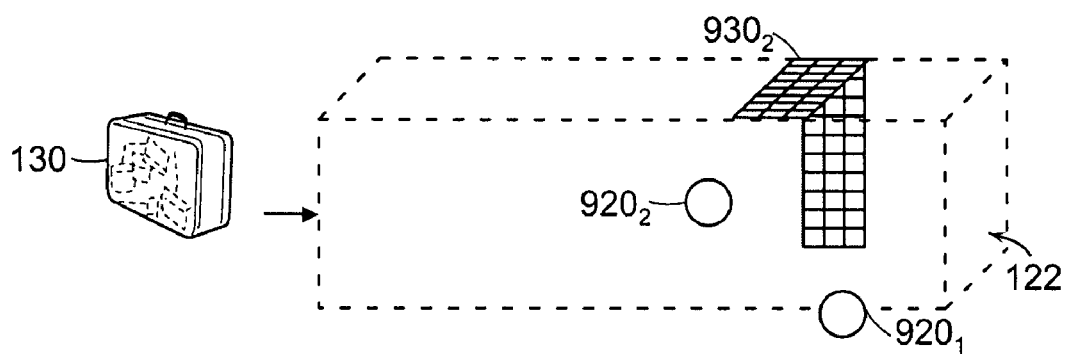

FIG. 9B illustrates an alternative way in which the number of attenuation measurements may be increased. In the example shown, multiple sources $920_1$ and $920_2$ are positioned to irradiate an L-shaped detector array $930_2$. The detector array $930_2$ differs from the detector array $930_1$ (FIG. 9A) in that the detector array $930_2$ includes multiple rows of detectors. In various embodiments, any or all of the detector arrays in an inspection system may employ such a multi-row configuration. In the illustrated example, three rows of detectors are shown. It should be appreciated, however, that any suitable number of rows of detectors may be incorporated in a detector array. In such a configuration, each row of detectors will have a different angular position relative to each of the sources $920_1$ and $920_2$. Accordingly, rays from the sources $920_1$ and $920_2$ reaching each row of the detector array $930_2$ will pass through different voxels of an item under inspection and represent a different measurement. In addition, although the respective rows of detectors in the example shown are illustrated as being disposed directly adjacent one another in the array, it should be appreciated that the rows may alternatively be separated from one another by an appropriate distance. Such a configuration may be desirable, for example, to minimize motion artifacts.

Figure 9C:
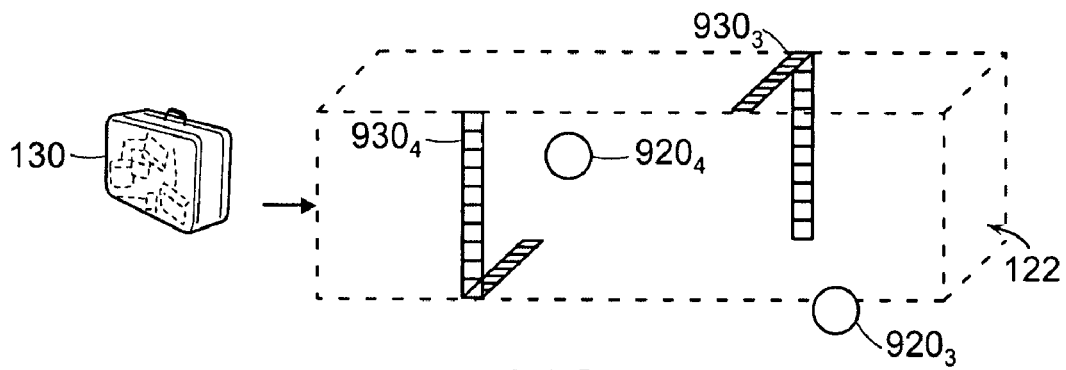

FIG. 9C shows another possible technique to increase the number of measurements on an item under inspection. In this example, two L-shaped detector arrays $930_3$ and $930_4$ are provided, and sources $920_3$ and $920_4$ are positioned opposite the detector arrays $930_3$ and $930_4$, respectively, so as to illuminate those arrays. As shown, the L-shaped detector arrays $930_3$ and $930_4$ may be positioned on opposite sides of the tunnel 122 so that the rays emitted by the two sources $920_3$ and $920_4$ will intercept the item under inspection from opposite sides. Accordingly, rays passing from the sources to the detectors pass through an item under inspection within the tunnel 122 from significantly different angles. The range of angles collectively spanned by the rays between the source $920_3$ and the detector array $930_3$ and the source $920_4$ and the detector array $930_4$ will be about twice the range of angles spanned by rays from a single source to a single detector array. It should be appreciated that other sources and/or detectors may additionally or alternatively be positioned at different locations about the tunnel so as to provide additional or different angular coverage.

Figure 9D:
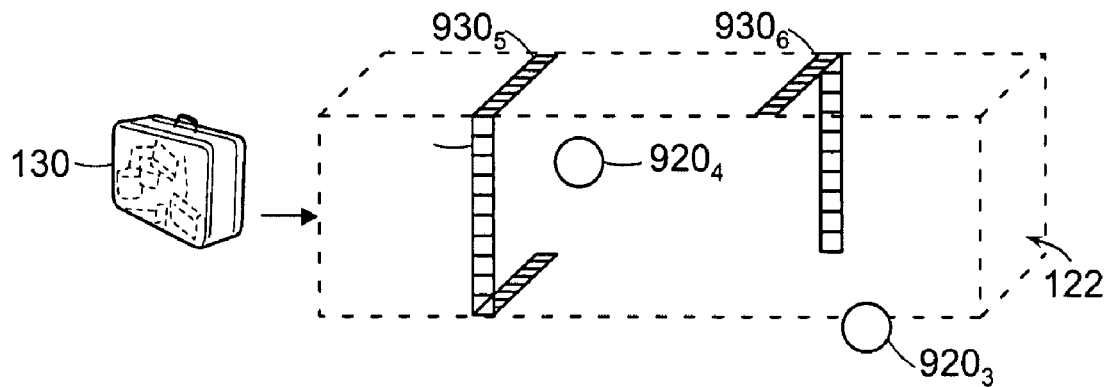

FIG. 9D shows yet another possible technique that may be employed to increase the range of angles spanned by rays passing through the item under inspection. In this example, a detector array $930_5$ is formed with segments that span a larger amount of the periphery of the tunnel 122 than a corresponding detector array $930_6$. In the embodiment of FIG. 9D, the detector array $930_5$ is C-shaped. In various embodiments, any or all of the detector arrays in an inspection system may employ such a configuration.

Figure 9E:
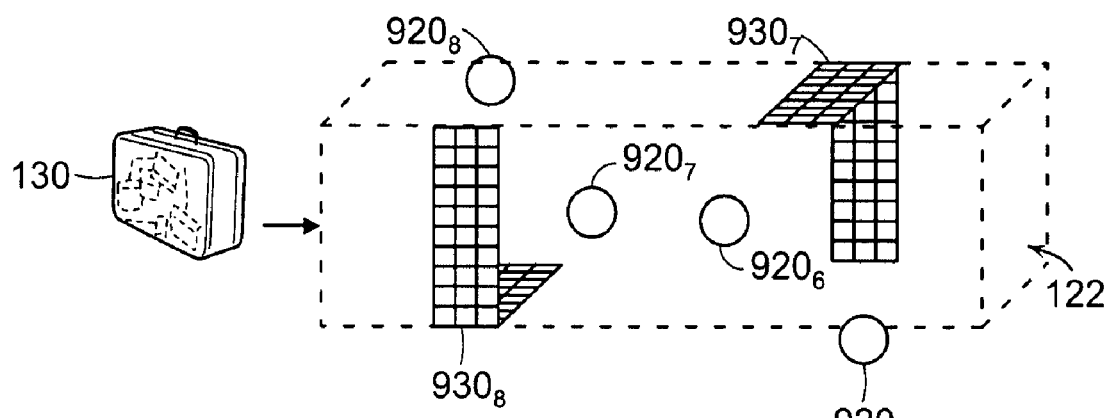

FIG. 9E illustrates yet another example of a technique that may be employed to increase the range of angles spanned by rays passing through the item under inspection. This example is essentially a combination of the techniques discussed above in connection with FIGS. 9B and 9C. In particular, in the example shown, two multi-row detector arrays $930_7$ and $930_8$ are positioned on opposite sides of the tunnel 122, with the detector array $930_8$ being illuminated by a first pair of skewed sources $920_5$ and $920_6$, and the detector array $930_8$ being illuminated by a second pair of skewed sources $920_7$ and $920_8$.

The approaches illustrated in FIGS. 9A-E may be used separately or together. In addition, it should be appreciated that any or all of the approaches described in connection with FIGS. 9A-E, and elsewhere herein, may be combined with the approach discussed above in connection with FIGS. 8A-B, so that discrete measurements may be taken from the respective detectors at many different times as a conveyor 120 moves an item under inspection 130 through an inspection system 110.

In some embodiments, multiple detector arrays are employed. For example, four L-shaped detector arrays may be used, with each L-shaped array having a vertex positioned along one of four edges of the tunnel 122. Such detector arrays may have multiple rows of detectors. For example, each detector array may have "12" rows of detectors. Further, each detector array may have associated with it multiple sources. For example, each of the four detector arrays may have two sources associated with it.

Figure 10:
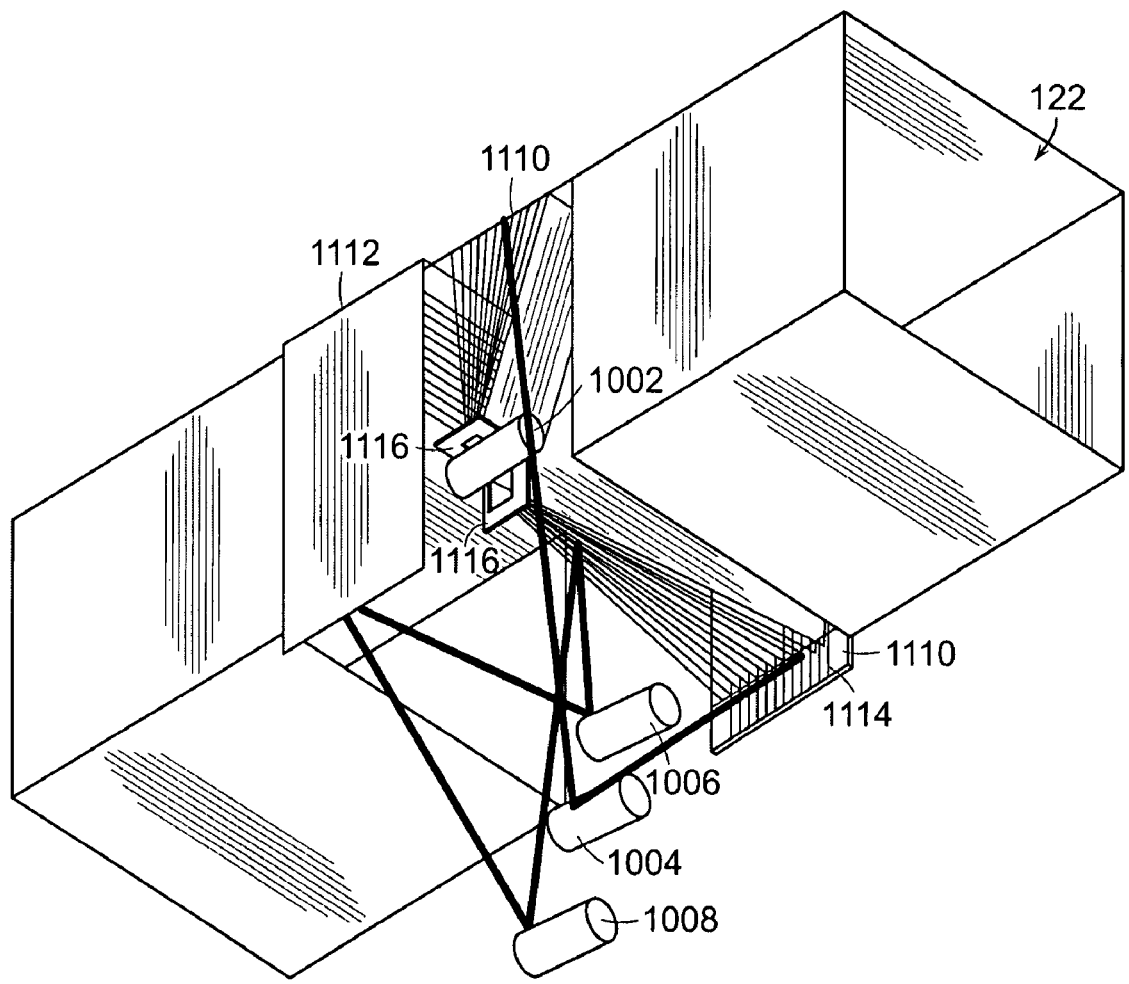
FIG. 10 is a drawing illustrating various components of an illustrative example of an inspection system.
Figure 11C:
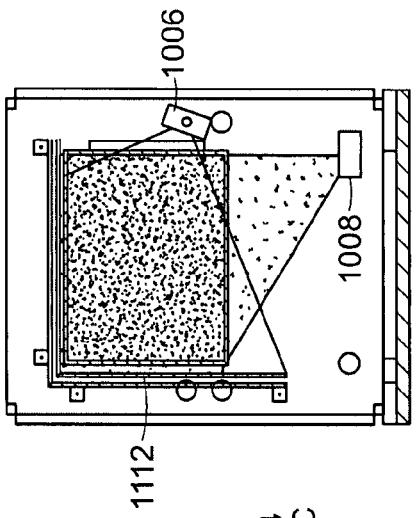
FIG. 11C is a drawing showing a cross-section of the inspection system shown in FIG. 11A taken through the line B-B.
Figure 11A:
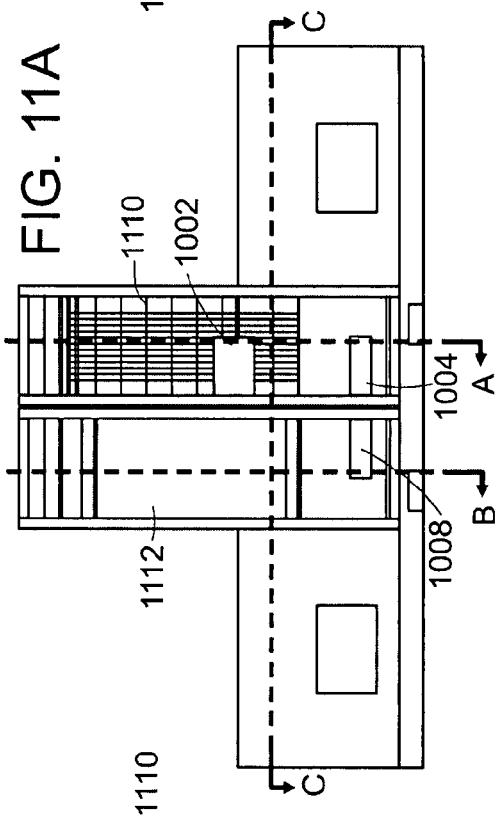
FIG. 11A is a drawing illustrating, in more detail, a side-view of the inspection system shown in FIG. 10.
Figure 11B:
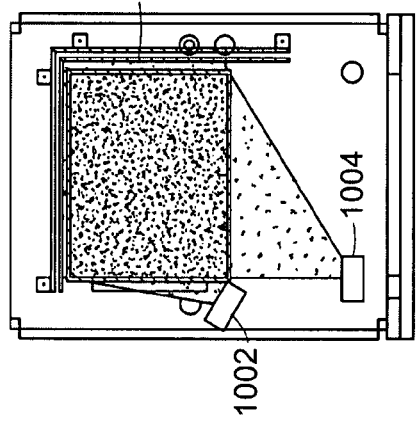
FIG. 11B is a drawing showing a cross-section of the inspection system shown in FIG. 11A taken through the line A-A.
Figure 11D:
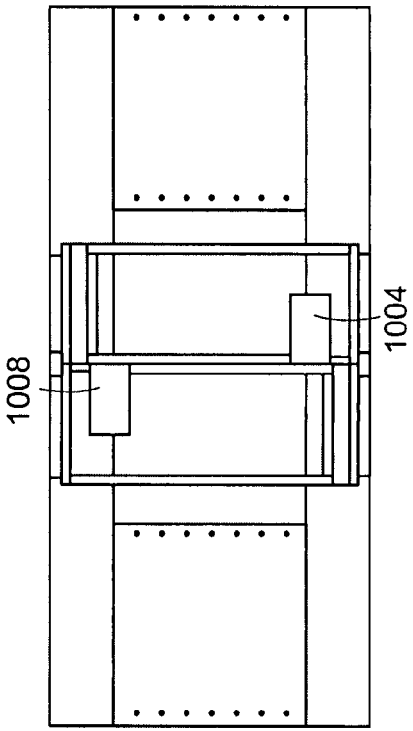
FIG. 11D is a drawing showing a cross-section of the inspection system shown in FIG. 11A taken through the line C-C.

FIG. 10 shows a perspective view of various components of an illustrative example of an inspection system that may embody certain inventive features disclosed herein. FIGS. 11A-D illustrate in more detail how the various components shown in FIG. 10 may be configured and arranged. FIG. 11A is a side view of the example system. FIGS. 11B, 11C, and 11D are cross-sectional views taken through sections A-A, B-B, and C-C, respectively, of FIG. 11A. The described inspection system may, for example, make attenuation measurements $D_i$ that may be used to obtain a volumetric density image I of an item under inspection, as described above.

In the example shown in FIGS. 10 and 11, the inspection system comprises four distinct radiation sources 1002, 1004, 1006, 1008. As shown, a first pair of skewed radiation sources 1002, 1004 is positioned so as to illuminate a first bank of detectors 1110, and a second pair of skewed radiation sources 1006, 1008 is positioned so as to illuminate a second bank of detectors 1112. In this example, each of the detector banks 1110, 1112 comprises twelve separate rows of detectors. One such row is identified in FIG. 10 with the reference numeral 1114. It should be appreciated that each row of detectors may itself comprise hundreds of detectors, each capable of making an attenuation measurement for a particular ray passing through the item under inspection. Although shown only for the source 1002 in FIG. 10, each of the sources 1002, 1004, 1006, 1008 may have associated with it a respective collimator 1116. Each such collimator may be configured and arranged to collimate the x-rays or other form of radiation generated by its associated source into a number of fan beams equal to the number of detector rows it illuminates. Thus, in the example embodiment shown, each collimator forms twelve fan beams, with each such beam being directed toward a respective row of detectors, e.g., row 1114.

In the example shown, the banks of detectors 1110, 1112 are offset from one another along the length of the tunnel 122. Since each of the four sources 1002, 1004, 1006, 1008 is capable of taking "12" skewed tomographic views in this example, a total of "48" skewed tomographic views may be taken of an item under inspection for every position of the conveyor at which attenuation measurements are made. When single energy measurements are made, two samples may be taken at each conveyor position, one for each of the two sources associated with each detector array. When dual-energy measurements are taken, four samples may be taken at each conveyor position, with both a high-energy and a low energy sample being taken for each of the two sources associated with each detector array. Known techniques may be employed to compensate for the motion of the conveyor between the taking of groups of samples that are intended to be for the same conveyor position.

Figure 12:
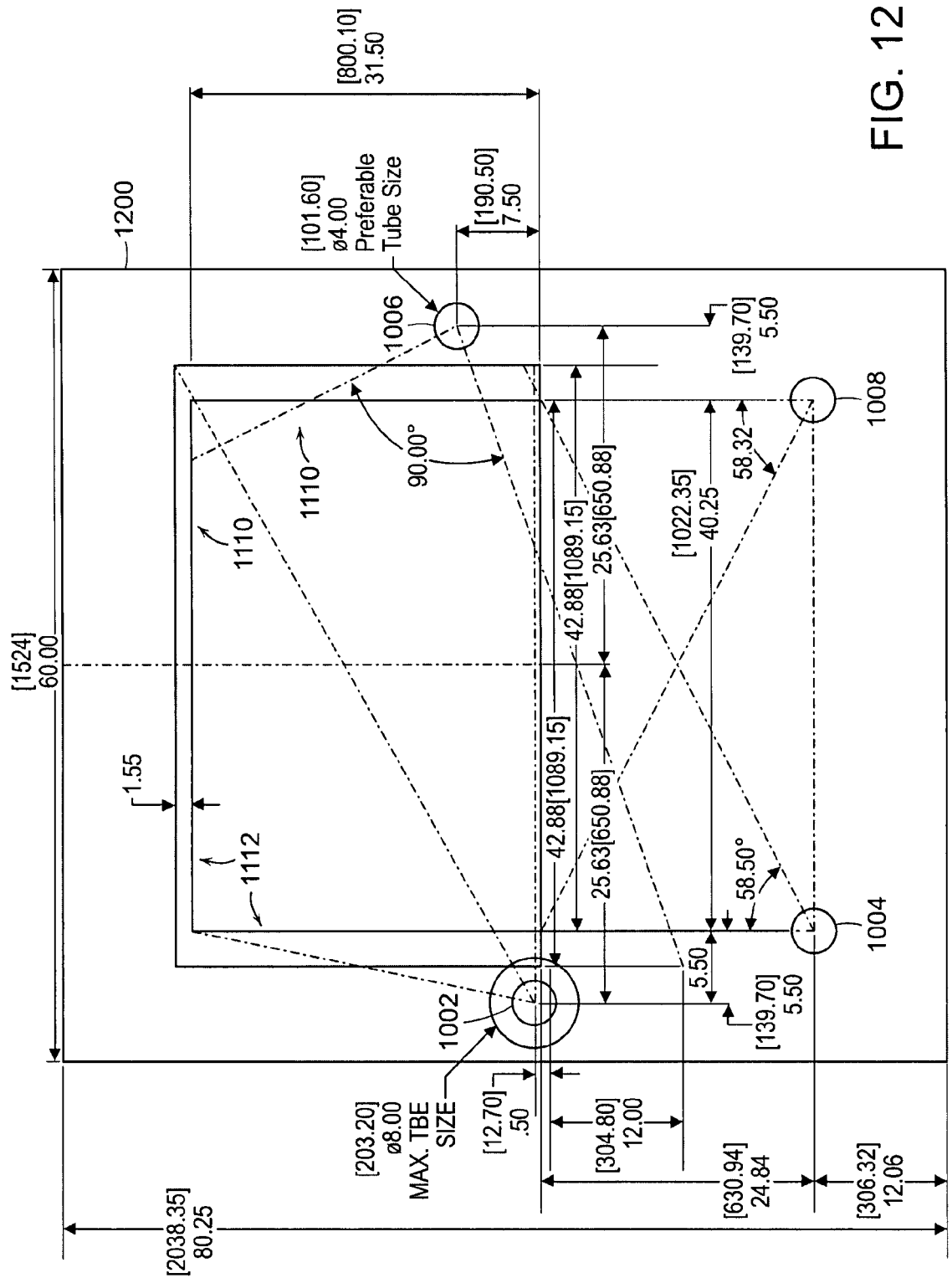
FIG. 12 is a schematic drawing showing various dimensions of the inspection system shown in FIGS. 10 and 11.

FIG. 12 shows in greater detail how the sources 1002, 1004, 1006, 1008 and detector banks 1110, 1112 may be positioned with respect to one another within a frame envelope 1200 of the inspection system, and the range of angles over which each source 1002, 1004, 1006, and 1008 may provide rays illuminating its associated detector bank. In FIG. 12, the linear measurements in brackets are in millimeters and those not in brackets are in inches.

Figure 13:
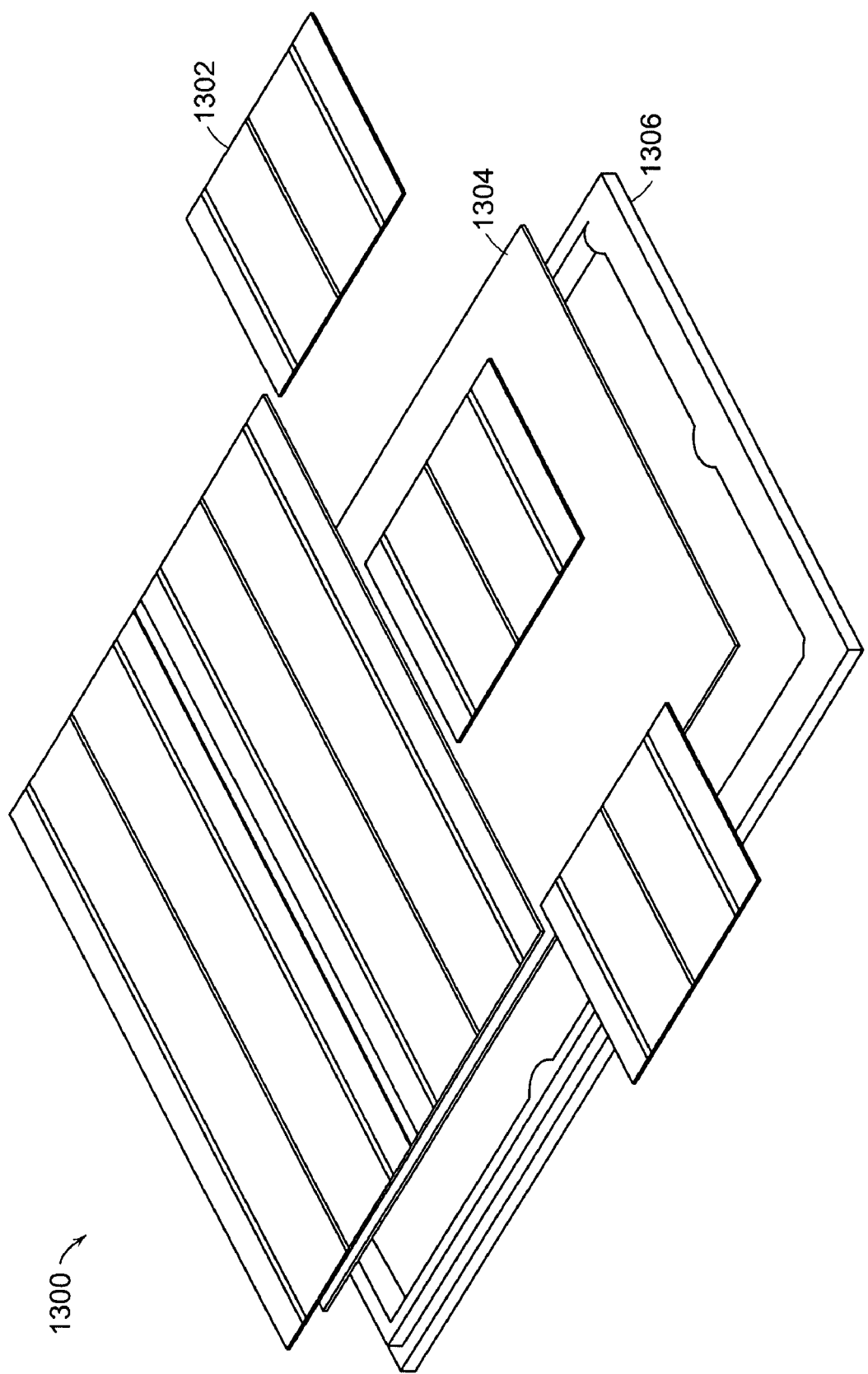
FIGS. 13 and 14 are drawings illustration how detector banks suitable for use in the example embodiment described in connection with FIGS. 10-12 may be configured.

FIGS. 13 and 14 illustrate an example of how detector banks suitable for use in a system such as that described above may be configured. As shown in FIG. 13, several individual scintillator/detector boards 1302 may be mounted on a motherboard 1304. The motherboard 1304, in turn, may be secured to an alignment frame 1306, thus forming an x-ray detection assembly 1300. The alignment frame 1306 may aid with the registration of the detector arrays.

Detectors may be arranged on the scintillator/detector boards 1302 in any of numerous ways, and the invention is not limited to any particular arrangement. In some embodiments, for example, each scintillator/detector board 1302 may comprise three rows of detectors, with each outer row comprising "32" separate detectors having a width of three millimeters, and the middle row comprising "64" separate detectors having a width of "1.5" millimeters. In such an embodiment, each detector/scintillator board 1302 would thus comprise "128" separate detectors, each capable of making a distinct attenuation measurement $D_i$, as discussed above. In the example shown in FIG. 13, the x-ray detection assembly 1300 includes a total of "9" scintillator/detector boards 1302. Accordingly, in this example each detector bank comprises "9" detector rows. The detectors may be made of any of a number of suitable materials, and the invention is not limited to the use of any particular detector material. The detectors may measure spectral properties and/or total energy. In some embodiments, for example, the detectors may be made of cadmium tungstate ($CdWO_4$).

Figure 14B:
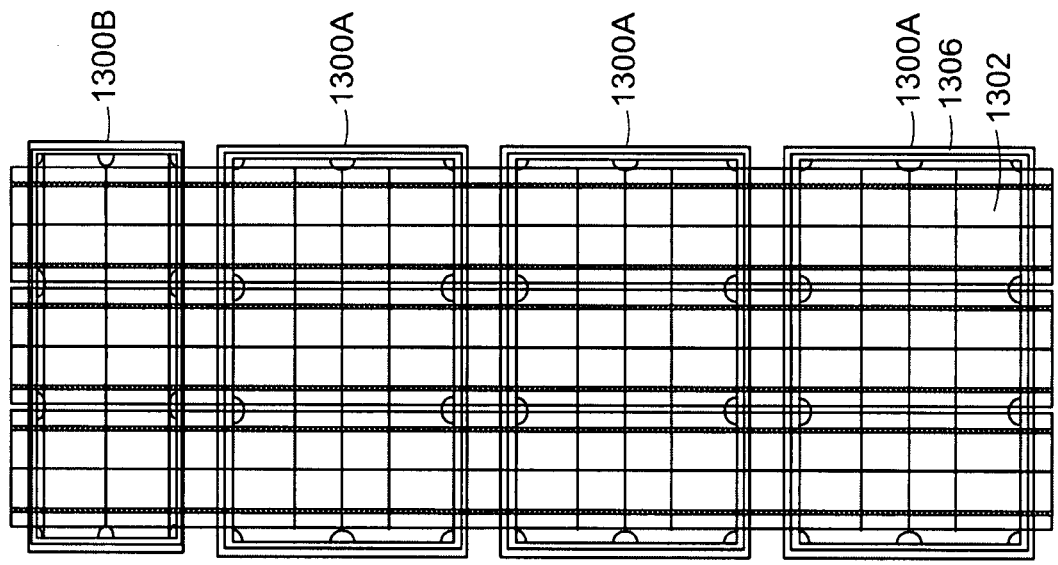
Figure 14A:
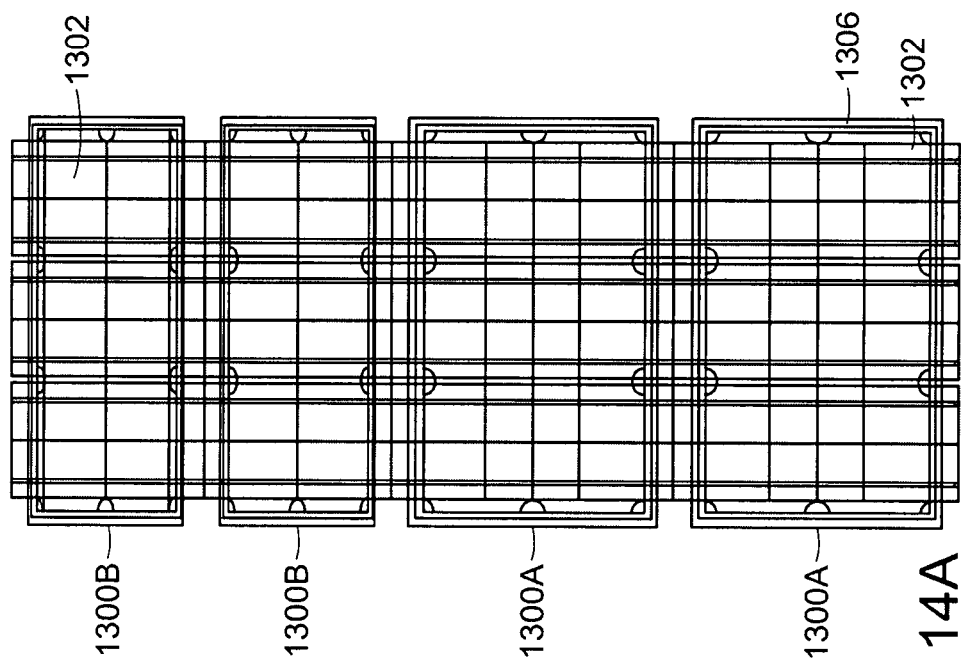

FIGS. 14A-B illustrate how several x-ray detection assemblies 1300 can be assembled together to form portions of detector banks like the detector banks 1110, 1112 discussed above. For example, the group of four x-ray detection assemblies 1300 shown in FIG. 14A may form one leg of each of the L-shaped detector banks 1110, 1112, and each of the other legs of those detector banks may be formed by a group of four x-ray detection assemblies 1300 like that shown in FIG. 14B. The only difference between the structures of FIGS. 14A and B is that the structure of FIG. 14A comprises "2" x-ray detection assemblies 1300A (each including "9" detector/scintillator boards) and "2" x-ray detection assemblies 1300B (each including "6" detector/scintillator boards), whereas the structure of FIG. 14B comprises "3" x-ray detection assemblies 1300A and "1" x-ray detection assemblies 1300B. The structure of FIG. 14B is thus slightly longer than that of FIG. 14A.

It should be appreciated that, in some embodiments, the detectors that are employed need not be arranged in straight lines and may additionally or alternatively be arranged in arcs or in other arrangements.

As is evident from a study of FIG. 12, a significant number of points in the image space that is examined by the example system described in FIGS. 10-12 fall outside of the convex hull of the set of sources the system uses to create images, and also fall outside of the convex hull of the (virtual) set of sources reflected through the isocenter of the image space. Accordingly, when a three-dimensional tomographic image is created with attenuation data accumulated with sources and detectors arranged as shown, and using one or more of the techniques described above, an image may be created for which it is impossible to find any vector in the image for which all source-detector ray directions form an angle between "85" and "95" degrees with the vector. In other words, such an inspection apparatus may form a tomographic image, in which, for all possible orientations of a three dimensional plane, the orientation vectors of at least some of the rays of radiation for which transmission data was accumulated and used to form the tomographic image form an angle of less than eighty-five degrees or greater than ninety five degrees with respect to the plane.

Nevertheless, the use of the above-described parallel implementation of an iterative algorithm for forming a tomographic image based on the data acquired by such a system allows the system to accurately reconstruct sheet-like objects at arbitrary orientations. The systems and techniques described above allow, in some embodiments, the reconstruction of a three dimensional tomographic image having a half-width-half-maximum (HWHM) resolution that is substantially less than 5 millimeters in all directions.

Though using multiple sources to illuminate each detector array reduces the number of detectors required to construct an inspection system, interference between sources may result. It may thus be desirable to sequence the operation of the sources associated with the same detector array so that, at any time, each detector array is irradiated with rays from no more than one of the sources.

Figure 15:
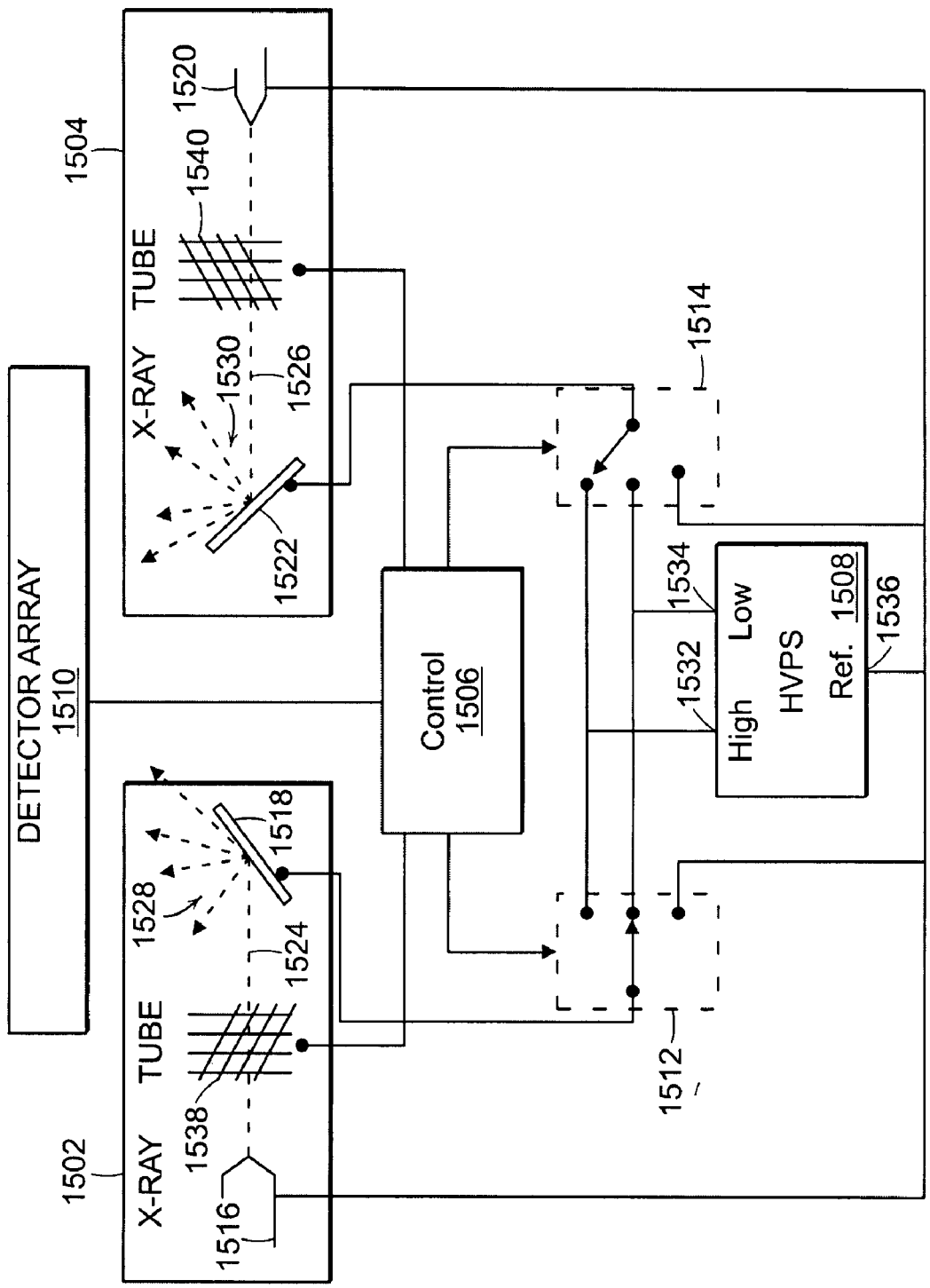
FIG. 15 is a schematic diagram of an example of a system employing a pair of gridded dual energy x-ray tubes to illuminate a common detector array.

FIG. 15 shows an illustrative example of an x-ray generation system that may embody certain inventive features disclosed herein. As shown, the system comprises a pair of x-ray tubes 1502 and 1504, a high-voltage power supply 1508, and associated control circuitry 1506. As discussed below, the tubes 1502 and 1504 may be configured and arranged to selectively generate x-rays that illuminate a common detector array 1510. One or more x-ray generation systems like that shown may, for example, be used in inspection systems such as those described above. The tubes 1502 and 1504 may, for example, correspond to the pair of sources 1002 and 1004 in the embodiment of FIGS. 10-12 discussed above. In such a case, the detector array 1510 would thus correspond to the detector bank 1110 in that same embodiment. The same or a similar type of x-ray generation system may also, of course, be employed to form the separate pair of sources 1006 and 1008 described above, with the detector array 1510 likewise corresponding to the detector bank 1112 in such a case. Similarly, the tubes 1502, 1504 and detector array 1510, and the techniques described herein, may correspond with the source/detector combinations and imaging techniques described above in connection with FIGS. 8 and 9.

The foregoing examples should not be deemed as limiting, however. Rather, it should be appreciated that the circuitry and techniques shown and described may provide a benefit in any circumstance where high-speed dual-energy radiation generation is desired. Although only two x-ray tubes are shown and described, it should be appreciated that any number of x-ray tubes, or other types of radiation generating elements, may be constructed and controlled as illustrated and described below in alternative embodiments. Moreover, it should be appreciated that it is not critical that more than one x-ray tube, or other type of radiation generating element, be employed in all circumstances, as a single gridded, dual-energy tube like that described may find applications in any of numerous other environments.

As shown, a pair of switches 1512, 1514 are provided to allow the control circuitry 1506 to independently control the voltage levels that are applied across the two x-ray tubes 1502, 1504. Although the tubes 1502 and 1504 in the example shown are constructed in the same fashion, it is not critical that the tubes be identical. In alternative embodiments, tubes of different types or construction may be employed. For instance, in some embodiments, the two or more tubes that are employed may generate different types of radiation. In the illustrated example, the tubes 1502, 1504 are skewed so that they to irradiate a single detector array 1510 from different angles. It should be appreciated, however, that one or more tubes and related circuitry like that shown may additionally or alternatively be configured and operated to irradiate one or more additional or different detectors, detector arrays, or detector banks in alternative embodiments.

In FIG. 15, the x-ray tube 1502 is illustrated schematically by a cathode 1516 and a target 1518, and the x-ray tube 1504 is similarly illustrated schematically by a cathode 1520 and a target 1522. As in a conventional x-ray source, the cathodes 1516, 1520 may emit beams 1524, 1526 of electrons. Either of the x-ray tubes 1502, 1504 may be caused to emit radiation 1528, 1530 by placing a high voltage between the cathode 1516, 1520 and the target 1518, 1522 of that tube. The high voltage causes the electrons in the corresponding beam 1524, 1526 to accelerate towards its associated target 1518, 1522. When the electrons impact the target 1518, 1522, they have sufficiently high energy to cause the target 1518, 1522 to emit radiation in the form of x-rays.

The energy of the radiation 1528, 1530 emitted from the targets 1518, 1522 is proportional to the potential difference between the targets 1518, 1522 and the cathodes 1516, 1520. In the embodiment of FIG. 15, the high-voltage power supply 1508 generates a high voltage, e.g., 150 KVolts (relative to a voltage at a reference node 1536), at a first output 1532, and also generates and a lower voltage, e.g., 75 KVolts (relative to the voltage at the reference node 1536), at a second output 1534. As shown, the reference output 1508 may be connected to each of the cathodes 1516, 1520, and each of the switches 1512, 1514 may be configured to connect a selected one of the supply outputs 1532, 1534 to a corresponding one of the targets 1518, 1522, thereby allowing a selected one of the high voltage and the low voltage to be applied between the cathode 1516, 1520 and target 1518, 1522 of either x-ray tube 1502, 1504. In addition, each of the switches 1512, 1514 may have a third position in which no potential difference is applied between the corresponding cathode 1516, 1520 and target 1518, 1522. When either of the switches 1512, 1514 is in such a position, the corresponding x-ray tube 1502, 1504 is effectively off.

In situations, such as several of those described above, where multiple x-ray tubes 1502, 1504 are used to illuminate the same detector array 1510, it may be desirable to stop one of the tubes 1502, 1504 from generating x-rays during those periods when the detector array 1510 is accumulating and outputting data based on radiation from the other source. One way that could be accomplished is by selectively switching off the x-ray tubes 1502, 1504 by placing the switches in their third positions in which no potential is applied between the cathodes 1516, 1520 and targets 1518, 1522. While suitable for some applications, that technique may be too slow for some applications due to the transient periods involved. In the example embodiment shown in FIG. 15, each of the x-ray tubes 1502, 1504 advantageously includes a mechanism for selectively steering or redirecting its electron beam 1524, 1526 so that it does not reach its target 1518, 1522 without requiring either the high or low voltage from the power supply 1508 to be removed from between its cathode 1516, 1520 and target 1518, 1522.

Such steering or redirecting of the electron beams 1524, 1526 could be accomplished in any of a number of ways, and the invention is not limited to any particular mechanism or technique for accomplishing such a result. In the embodiment shown, a pair of grids 1538, 1540 are employed for such a purpose. As shown, each of the grids 1538, 1540 may be disposed in the path between one of the cathodes 1516, 1520 and its corresponding target 1518, 1522. Any suitable method may be used to control the grids 1538, 1540. In some embodiments, for example, the grids 1538, 1540 may be selectively grounded to shunt the electrons in the beams 1524, 1526 away from the targets 1518, 1522. In other embodiments, the grids 1538, 1540 may be raised to a potential higher than that of the targets 1518, 1522, which may also interrupt the beams 1524, 1526. In any event, the control circuitry 1506 may somehow selectively control the operation of the grids 1538, 1540 so as to either allow the associated electron beam 1524, 1526 to pass through the grid 1538, 1540, or to inhibit the associated electron beam 1524, 1526 from reaching its target 1518, 1522.

The control circuitry 1506 may control the timing of both the acquisition of data from the detector array 1510 and the generation of radiation from the x-ray tubes 1502, 1504. For example, during a first phase, the control circuitry 1506 may control the grid 1538 so that the x-ray tube 1502 generates radiation 1528, and may also control the detector array 1510 so that the detectors in the array measure the intensity of the radiation that is received during that same phase. The position of the switch 1512, as determined by the control circuitry 1506, may determine whether the generated radiation 1528 from the tube 1502 has a high energy or a low energy. After such a phase, the grid 1538 may be controlled so that the x-ray tube 1502 ceases generating radiation. During a subsequent phase, the control circuitry 1506 may control the detector array 1510 to output the intensity values measured by the detectors, so as to allow attenuation measurements to be made based upon those outputs. Once the outputs of the detector array 1510 have been measured, the control circuitry 1506 may then control the grid 1540 so that the x-ray tube 1504 generates radiation 1530, and may also control the detector array 1510 so that the detectors in the array measure the intensity of the radiation 1530 that is received from the x-ray tube 1504. As with the tube 1502, the position of the switch 1514, as determined by the control circuitry 1506, may determine whether the generated radiation 1530 from the tube 1504 has a high energy or a low energy. The control circuitry may then control the grid 1540 so that the x-ray tube 1504 ceases generating radiation, after which time the control circuitry 1506 may control the detector array 1510 to output the intensity values measured by the detectors, so as to allow attenuation measurements to be made based upon those outputs. The process may repeat in this fashion, alternating between measurements from the x-ray tubes 1502 and 1504 (by properly controlling the grids 1538, 1540), and/or alternating between high and low energy measurements for each such tube (by properly controlling the switches 1512, 1514).

Thus, in embodiments in which dual energy measurements are made from two skewed sources, the alternating pattern may involve a sequence including four separate radiation generation phases, with one of the two sources generating either high or low radiation during each such phase. The various forms of radiation for exciting the detector array 1510 may be applied in any of a number of possible sequences, and the invention is not limited to any particular order. In some embodiments, for example, the control circuitry 1506 may control the switches 1512, 1514 and grids 1538, 1540 so as to cause the tubes 1502, 1504 to generate radiation in the following repeating sequence (1) high energy radiation from the tube 1502, (2) low energy radiation from the tube 1502, (3) high energy radiation from the tube 1504, and (4) low energy radiation from the tube 1504. In other embodiments, the control circuitry 1506 may, for example, control the switches 1512, 1514 and grids 1538, 1540 so as to cause the tubes 1502, 1504 to generate radiation in the following repeating sequence (1) high energy radiation from the tube 1502, (2) high energy radiation from the tube 1504, (3) low energy radiation from the tube 1502, and (4) low energy radiation from the tube 1504. Other similar patterns are also possible.

Figure 16:
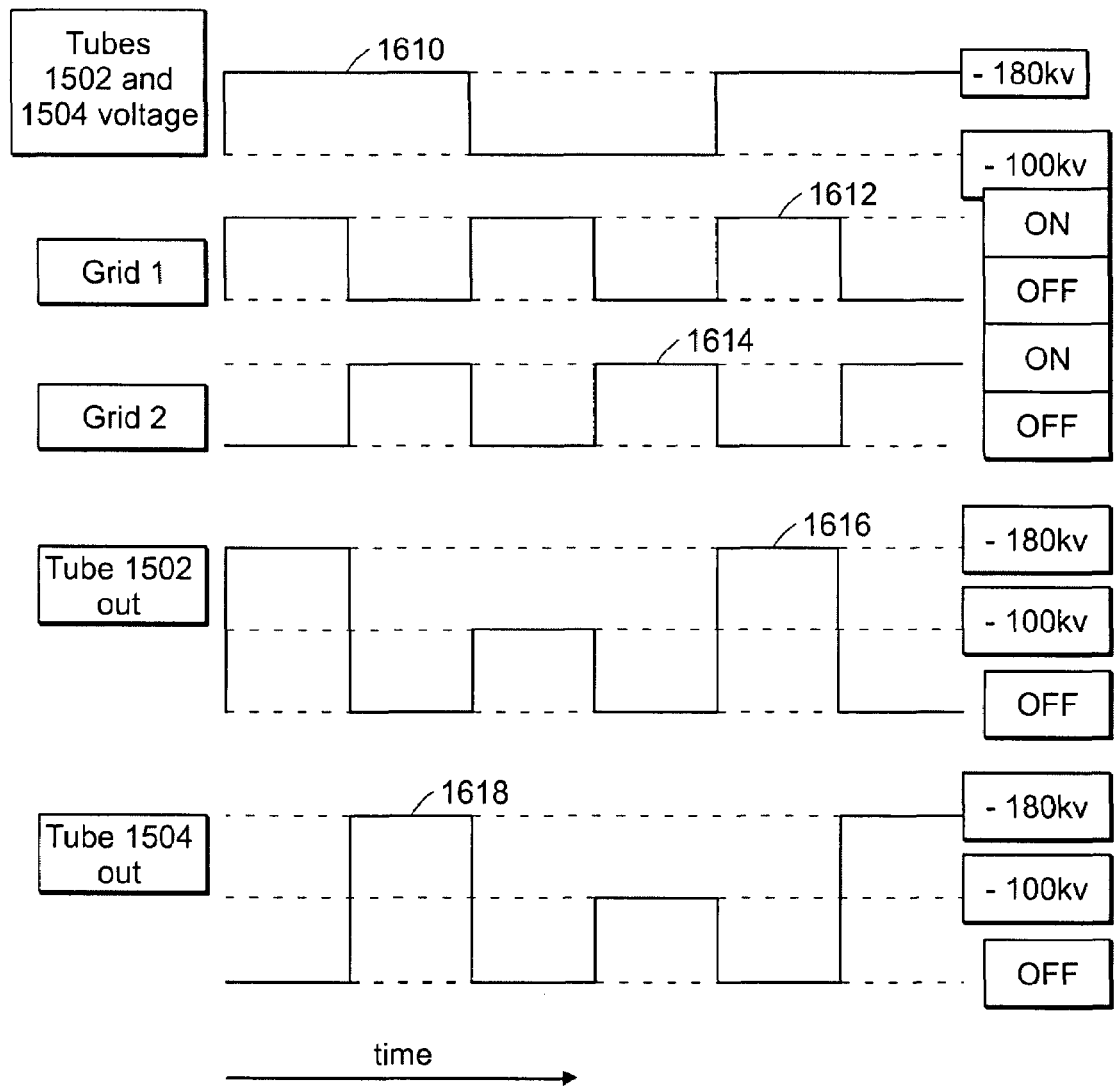
FIGS. 16 and 17 are timing diagrams illustrating examples of various waveforms that may appear in the system shown in FIG. 15.
Figure 17:
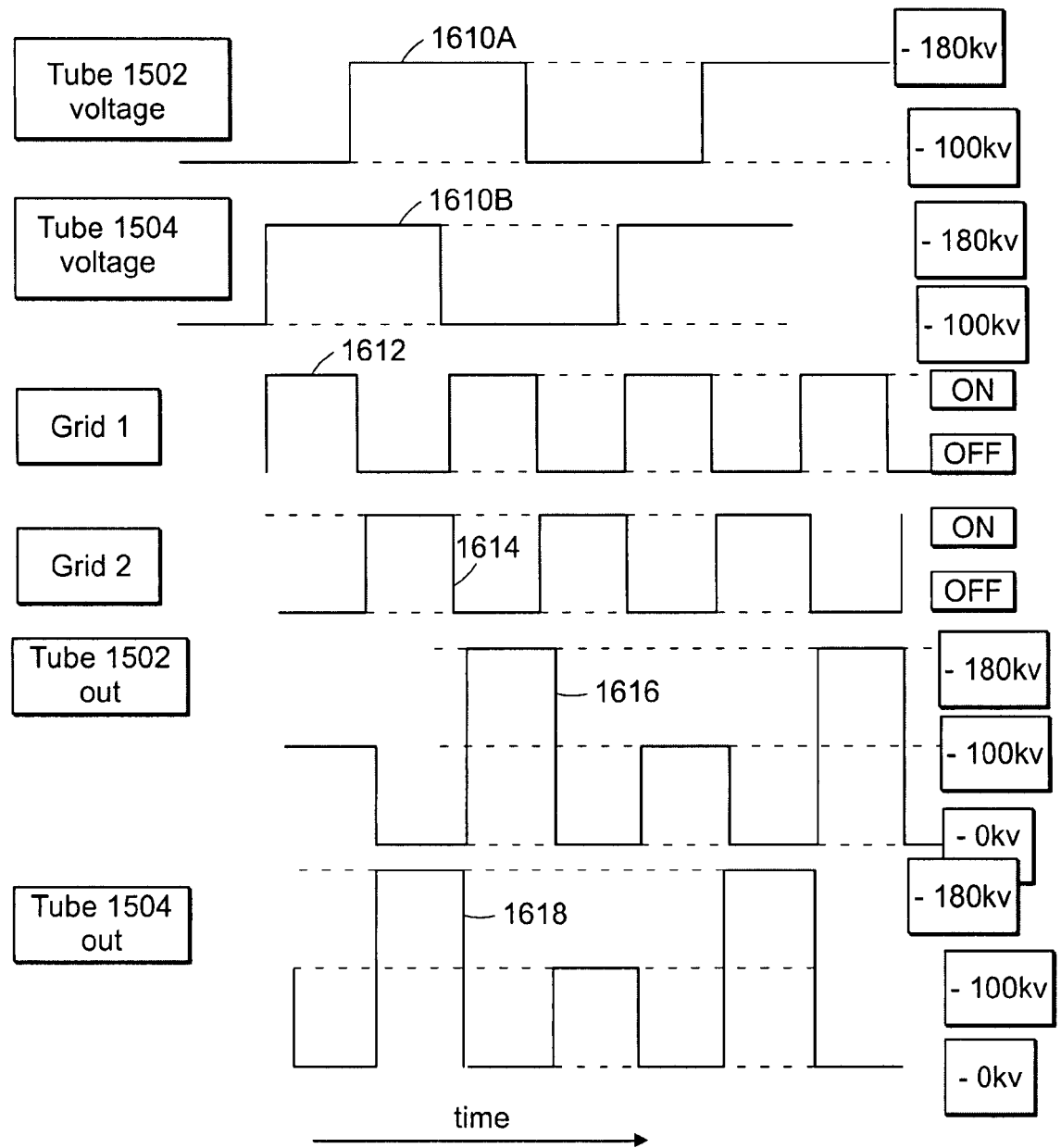

The timing diagrams of FIGS. 16 and 17 illustrate two examples of how the control circuitry 1506 may control the switches 1512, 1514 and grids 1538, 1540 to cause the x-ray tubes 1502, 1504 to selectively generate high and low energy radiation in suitable patterns. As shown, both timing diagrams include a waveform 1610 or waveforms 1610A, 1610B which represent the voltages applied to the tubes 1502, 1504 (between the respective cathodes 1516, 1520 and targets 1518, 1522). Both diagrams further include waveforms 1612 and 1614 which represent whether the grids 1538 and 1540, respectively, are "on" or "off." Finally, both diagrams include waveforms 1616 and 1618 which represent the voltages that are applied to the tubes 1502 and 1504, respectively, during periods when they emit radiation.

In the example of FIG. 16, because the same voltage is applied to both tubes 1502, 1504 at all times, it would not be necessary to employ two separate switches 1512, 1514 to control the application of high and voltages to the tubes. Thus, in embodiments that employ such a technique, a single switch may control whether both targets 1518, 1522 are connected to either the "high" output 1532 or the "low" output 1534 of the power supply 1508. In the example of FIG. 17, however, the voltages applied to the x-ray tubes 1502, 1504 are different at different times. The use of two separate switches 1512, 1514 in such a situation allows the voltages applied to the tubes to be separately controlled in such a manner. In FIG. 17, the waveform 1610A may thus represent the voltage applied to the tube 1502 via the switch 1512, and the waveform 1610B may represent the voltage applied to the tube 1504 via the switch 1514.

In embodiments where different groups of sources are used to illuminate respective detector arrays, such as the embodiment described above in connection with FIGS. 10-12, the voltage 1610 that is applied to the x-ray tubes used to illuminate one detector array (or bank of detector arrays) may be controlled so as to be out of phase with the voltage applied to the x-rays tubes used to illuminate the other detector array (or bank of detector arrays), so that both sets of tubes will not emit high-energy radiation at the same time, thus minimizing the total amount of radiation that is emitted by the system at any one time.

The duration of time for which each of the tubes 1502, 1504 is emitting radiation may depend on the characteristics of the detector array 1510. Circumstances may exist in which the access time to collect the measurements from the detector array 1510 is relatively long. For example, in some circumstances, "10" milliseconds to collect the outputs from the detector 1510 may be considered a relatively long time interval because in such an interval an item under inspection may move an appreciatable distance on the conveyor 120 (FIG. 1). As a result, if the detector array 1510 were illuminated continuously during this "10" millisecond acquisition interval, the acquired data would appear blurred, in much the same way that a photograph of a moving object may appear blurred. To avoid this blurring of the data used to form an x-ray image, each source may be controlled to turn on for a relatively small interval of time, for example, "1" millisecond, or "1/10" of the total acquisition interval, at the beginning of each acquisition interval.

In some embodiments, such abbreviated illumination intervals may be formed, for example, by using one of the switches 1512, 1514 to turn "on" and "off" one of the x-ray sources for the illumination interval period. In other embodiments, the grids 1538, 1540 may be employed for such a purpose. As noted above, the use of the grids 1538, 1540 may allow for faster switching than the use of the switches 1512, 1514. Thus, by incorporating the grids 1538, 1540 as control mechanisms, an inspection system employing an x-ray source as illustrated in FIG. 15 may be able to quickly switch between sources or energy levels with less blurring or other artifacts of the measured image.

By employing one or more x-ray generation systems configured and operated in a dual energy mode as described in connection with FIGS. 15-17 in an inspection system configured and operated as described above in connection with FIGS. 1-14, volumetric images can formed from the density of the item under inspection, the effective atomic number ($Z_{eff}$) of the item under inspection, or a combination of density and $Z_{eff}$.

Having thus described several aspects of at least one embodiment of this invention, it is to be appreciated that various alterations, modifications, and improvements will readily occur to those skilled in the art.

For example, the invention was illustrated by describing a system in which multiple views of an item under inspection are used to form a volumetric image. However, it should be noted that the sources and detector arrays used to make measurements for computing a volumetric image may additionally or alternatively be used to form one or more projection images.

In some embodiments, an inspection system such as described herein may perform multiple levels of inspection. For example, the system could be used in a first mode in much the same way that a convention multiview projection imaging system is used. If inspection of an item in multiview projection imaging mode did not result in clearing the item, the item could then be further inspected in the same equipment using a volumetric imaging mode.

In some embodiments, an inspection system such as described herein could operate in two modes, for example, by temporarily reversing the direction of the conveyor 120 after inspection of an item in the first mode. By reversing the direction of the conveyor, an item under inspection would be moved past the sources and detectors again and more data could be collected to allow formation of a volumetric image. Alternatively, all data needed to form either mutiview projection images or volumetric images could be collected at one time, but computations to perform a volumetric image could be performed only if projection imaging did not result in the item being cleared.

In some embodiments, some or all of the systems and techniques described above may be employed using gamma rays some other form of radiation in addition to or in lieu of x-rays. The sources that are employed in the various embodiments may be monochromatic, polychromatic, or may be operated at multiple energy points. In other embodiments, the x-ray sources that are employed may comprise fixed e-beam tubes that scan an extended target such as those described in U.S. Provisional App. Ser. No. 60/846,164, incorporated by reference above.

In some embodiments, an x-ray inspection system having some or all of the features described herein may use backscatter, forward scatter or side scatter data in addition to or in lieu of x-ray transmission data to obtain an image. In such a system, an image may be formed by combining transmission data with scattering data to allow for material discrimination.

In some embodiments, an obtained image may be combined with other sensor data, such as radar, microwave data and/or neutron response data, and/or trace detection to allow for material discrimination.

In some embodiments, some or all of the configurations and techniques described herein may be employed in a system where the sources and detector arrangements are fixed relative to one another on a gantry, and the gantry as a whole undergoes motion. Such motion of the gantry may be in addition to or in lieu of motion by a conveyor.

In some embodiments, an inspection system may comprise two or more dissimilar machines designed using configurations and techniques described herein where an item under inspection is passed from one machine to the other in the same orientation. In other embodiments, an inspection system may comprise two or more similar machines designed using configurations and techniques described herein where the orientation of an item under inspection is changed, e.g., rotated, between scans by the machines. In yet other embodiments, the same machine may be configured to scan the same item under inspection twice, e.g., by scanning in a forward direction and then reversing the direction of the conveyor and scanning in a backward direction, rotating the object between scans.

In some embodiments, an image may be formed, based upon data acquired using the configurations and techniques discussed above, using tomosynthesis in addition to or in lieu of iterative tomography.

The apparatus and techniques described herein may be used for any suitable purpose and need not be used for examination of luggage for contraband or explosives. For example, embodiments of the invention may additionally or alternatively be used for medical imaging and/or for non-destructive testing purposes.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface including keyboards, and pointing devices, such as mice, touch pads, and digitizing tables. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method for operating an inspection system, comprising steps of:
   (a) moving an item under inspection in a first direction relative to and at least partially between at least first and second radiation sources and at least some radiation detectors illuminated by the at least first and second radiation sources;
   (b) operating the at least first and second radiation sources and the at least some radiation detectors such that ray paths extending linearly between the at least first and second radiation sources and the at least some radiation detectors form acute angles with respect to a plane having a normal direction coinciding with the first direction that are substantially in excess of three degrees, the operating comprising illuminating at least some of the same radiation detectors of the at least some radiation detectors with each of first and second radiation sources; and
   (c) processing data accumulated by the at least some radiation detectors to form a three-dimensional tomographic data image of at least a portion of the item under inspection.

2. The method of claim 1, wherein the step (a) comprises using a conveyor to move the item under inspection relative to the at least first and second radiation sources and the at least some radiation detectors.

3. The method of claim 1, wherein the at least first and second radiation sources and the at least some radiation detectors remain stationary relative to a surface supporting the inspection system when the step (a) is performed.

4. The method of claim 1, further comprising a step of:
   (d) analyzing the image to ascertain whether the item under inspection contains an explosive or contraband.

5. The method of claim 1, wherein at least first and second radiation detectors of the at least some radiation detectors used to accumulate the data processed in the step (c) are positioned such that the first and second radiation detectors are substantially spaced apart in the first direction.

6. The method of claim 5, wherein the first and second radiation detectors are substantially non-contiguous such that a substantial gap exists between the first and second radiation detectors that is free of any radiation detectors.

7. The method of claim 1, wherein at least first and second radiation detectors of the at least some radiation detectors used to accumulate the data processed in the step (c) are substantially non-contiguous such that a substantial gap in the first direction exists between the first and second radiation detectors that is free of any radiation detectors.

8. The method of claim 1, wherein the step (c) comprises forming the three-dimensional tomographic image with a half-width-half-max resolution that is substantially less than five millimeters in all directions.

9. The method of claim 1, wherein the step (c) comprises forming the three-dimensional tomographic image using an iterative calculation technique.

10. The method of claim 1, further comprising:
    controlling the first and second radiation sources so that the first radiation source illuminates the at least some of the same radiation detectors of the at least some radiation detectors during first periods, and so that the second radiation source illuminates the at least some of the same radiation detectors during second periods that are substantially non-overlapping with the first periods.

11. The method of claim 1, wherein the step (b) further comprises operating the at least one radiation source and the radiation detectors such that ray paths extending linearly between the at least one radiation source and at least some of the radiation detectors form acute angles with respect to the plane that are substantially in excess of five degrees.

12. The method of claim 11, wherein the step (b) further comprises operating the at least one radiation source and the radiation detectors such that ray paths extending linearly between the at least one radiation source and at least some of the radiation detectors form acute angles with respect to the plane that are substantially in excess of ten degrees.

13. The method of claim 1, wherein the act of processing data comprises:
    determining an approximation, other than a multiple of a transpose, of an inverse of a system matrix for an inspection system;
    after determining the approximation, scanning an item under inspection to accumulate scan data for each of a plurality of rays through the item under inspection;
    computing an initial estimate of a volumetric image of the item under the inspection by combining the determined approximation of the inverse of the system matrix and the scan data; and
    employing an iterative process to refine the initial estimate of the volumetric image to obtain a more accurate volumetric image corresponding to the scan data.

14. An inspection system, comprising:
    a frame;
    at least one radiation source, supported by the frame, that emits rays of radiation;
    radiation detectors, supported by the frame, that are configured and arranged to detect rays of radiation emitted by the at least one radiation source;

a conveyor configured and arranged to move an item under inspection in a first direction relative to the frame such that at least a portion of the item under inspection passes between the at least one radiation source and at least some of the radiation detectors; and a processor configured to process data accumulated by the radiation detectors to form a three-dimensional tomographic data image of at least a portion of the item under inspection;

wherein the at least one radiation source and the radiation detectors are configured and arranged with respect to the conveyor such that ray paths extending linearly between the at least one radiation source and at least some of the radiation detectors form acute angles with respect to a plane having a normal direction coinciding with the first direction that are substantially in excess of three degrees, wherein:

the at least one radiation source comprises at least first and second radiation sources; and the inspection system further comprises a controller configured to control the first and second radiation sources so that the first and second radiation sources illuminate at least some of the same radiation detectors.

15. The inspection system of claim 14, wherein the processor is further configured to analyze the image to ascertain whether the item under inspection contains an explosive or contraband.

16. The inspection system of claim 14, wherein at least first and second ones of the radiation detectors are substantially spaced apart in the first direction.

17. The inspection system of claim 16, wherein the first and second ones of the radiation detectors are substantially non-contiguous such that a substantial gap exists between the first and second ones of the radiation detectors that is free of any radiation detectors.

18. The inspection system of claim 14, wherein at least first and second ones of the radiation detectors are substantially non-contiguous such that a substantial gap exists between the first and second ones of the radiation detectors that is free of any radiation detectors.

19. The inspection system of claim 14, wherein the processor is further configured to form a three-dimensional tomographic image with a half-width-half-max resolution that is substantially less than five millimeters in all directions.

20. The inspection system of claim 14, wherein the processor is further configured to form the three-dimensional tomographic image using an iterative calculation technique.

21. The inspection system of claim 14, wherein the controller is further configured to control the first and second radiation sources so that the first radiation source illuminates the at least some of the same radiation detectors during first periods, and so that the second radiation source illuminates the at least some of the same radiation detectors during second periods that are substantially non-overlapping with the first periods.

22. The inspection system of claim 14, wherein the at least one radiation source and the radiation detectors are configured and arranged with respect to the conveyor such that ray paths extending linearly between the at least one radiation source and at least some of the radiation detectors form acute angles with respect to the plane that are substantially in excess of five degrees.

23. The inspection system of claim 22, wherein the at least one radiation source and the radiation detectors are configured and arranged with respect to the conveyor such that ray paths extending linearly between the at least one radiation source and at least some of the radiation detectors form acute angles with respect to the plane that are substantially in excess of ten degrees.

24. An inspection system, comprising:

means for moving an item under inspection in a first direction relative to and at least partially between at least a first and second radiation sources and at least some radiation detectors illuminated by the at least one radiation source;

means for operating the at least first and second radiation sources and the radiation detectors such that ray paths extending linearly between the at least first and second radiation sources and at least some of the radiation detectors of the at least some radiation detectors form acute angles with respect to a plane having a normal direction coinciding with the first direction that are substantially in excess of three degrees;

means for processing data accumulated by the radiation detectors to form a three-dimensional tomographic data image of at least a portion of the item under inspection; and a controller configured to control the first and second radiation sources so that the first and second radiation sources illuminate at least some of the same radiation detectors.

25. The inspection system of claim 24, wherein:

the system further comprises means for determining an approximation, other than a multiple of a transpose, of an inverse of a system matrix for an inspection system; and the means for processing comprises:

means for computing an initial estimate of a volumetric image of the item under the inspection by combining the determined approximation of the inverse of the system matrix and the accumulated data; and means for employing an iterative process to refine the initial estimate of the volumetric image to obtain a more accurate volumetric image corresponding to the accumulated data.

* * * * *